United States Patent
Bennette et al.

(10) Patent No.: US 11,969,409 B2
(45) Date of Patent: *Apr. 30, 2024

(54) FORMULATIONS OF APREMILAST

(71) Applicant: AMGEN INC., Thousand Oaks, CA (US)

(72) Inventors: Nathan Bennette, Thousand Oaks, CA (US); William Brett Caldwell, Thousand Oaks, CA (US); Christi Hostetler, Thousand Oaks, CA (US); Kazden Ingram, Thousand Oaks, CA (US); Dory King, Thousand Oaks, CA (US); Kyle Kyburz, Thousand Oaks, CA (US); Alison Viles, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/196,718

(22) Filed: May 12, 2023

(65) Prior Publication Data

US 2023/0277502 A1 Sep. 7, 2023

Related U.S. Application Data

(63) Continuation of application No. 17/899,769, filed on Aug. 31, 2022, now Pat. No. 11,752,129, which is a continuation of application No. PCT/US2022/031325, filed on May 27, 2022.

(60) Provisional application No. 63/194,247, filed on May 28, 2021.

(51) Int. Cl.
*A61K 9/20* (2006.01)
*A61K 9/00* (2006.01)
*A61K 9/28* (2006.01)
*A61K 31/4035* (2006.01)

(52) U.S. Cl.
CPC ........ *A61K 31/4035* (2013.01); *A61K 9/0065* (2013.01); *A61K 9/2009* (2013.01); *A61K 9/2054* (2013.01); *A61K 9/2086* (2013.01); *A61K 9/2853* (2013.01); *A61K 9/2866* (2013.01)

(58) Field of Classification Search
CPC ........ A61K 9/14; A61K 9/145; A61K 31/154; A61K 31/145
See application file for complete search history.

(56) References Cited

U.S. PATENT DOCUMENTS

2017/0014367 A2 1/2017 Nilsson et al.
2017/0143671 A1* 5/2017 Hough ............... A61K 31/4035

FOREIGN PATENT DOCUMENTS

CZ 2018150 A3 4/2019
WO WO-0211702 A2 * 2/2002 ........... A61K 9/0004

OTHER PUBLICATIONS

Kevin J Edgar: "Cellulose esters in drug delivery", Cellulose, Kluwer Academic Publishers (Dordrecht), NL, vol. 14, No. 1, Sep. 6, 2006 (Sep. 6, 2006), pp. 49-64.
App. No. PCT/US2022/031325; International Search Report and Written Opinion dated Sep. 1, 2022.
Gazzaniga et al: "Oral pulsatile delivery systems based on swellable hydrophilic polymers", European Journal of Pharmaceutics and Biopharmaceutics, Elsevier Science Publishers B.V., Amsterdam, NL, vol. 68, No. 1, Nov. 30, 2007 (Nov. 30, 2007), pp. 11-18.
Zhang Qiangnan et al: "Development of an 1-59, amorphous based sustained release system 73-79 for apremilast a selective phosphodiesterase 4 (PDE4) inhibitor", International Journal of Pharmaceutics, vol. 615, Jan. 25, 2022 (Jan. 25, 2022), p. 121516.

* cited by examiner

*Primary Examiner* — Micah Paul Young
(74) *Attorney, Agent, or Firm* — MARSHALL, GERSTEIN & BORUN LLP

(57) ABSTRACT

Provided herein are oral dosage forms comprising a) a core tablet comprising (i) a drug layer comprising apremilast and hypromellose acetate succinate (HPMCAS) in an amorphous solid dispersion; and (ii) a swellable layer comprising one or more swellable polymers; and b) a coating layer disposed on the core tablet, wherein the oral dosage form surface comprises at least one drug release orifice. The disclosed oral dosage forms provide once-a-day dosing of apremilast and are suitable for treating diseases or disorders ameliorated by inhibiting phosphodiesterase subtype IV (PDE4).

19 Claims, 9 Drawing Sheets

FORMULATIONS OF APREMILAST

BACKGROUND

Apremilast is a phosphodiesterase subtype IV ("PDE4") inhibitor and has been approved worldwide for the treatment of various diseases associated with inflammation. For example, in the United States apremilast is approved for the treatment of adult patients with moderate to severe plaque psoriasis who are candidates for phototherapy or system therapy, for the treatment of adult patients with active psoriatic arthritis, and for the treatment of adult patients with oral ulcers associated with Behcet's Disease. Apremilast was the first, and remains the only, orally administered PDE4 inhibitor approved for the treatment of these inflammatory diseases. The recommended dosage for adult patients with active PsA and psoriasis is 30 mg twice daily (BID) orally, following a 5-day titration that is intended to reduce the gastrointestinal (GI) symptoms associated with initial therapy.

A goal in developing a drug is to provide dosage forms which make it possible to maintain a certain amount or concentration of drug in a subject's body that is clinically or therapeutically relevant. In some cases, this may not be achieved by traditional rapidly disintegrating tablets, as these tablets release the active ingredient contained therein all at once.

In view of the foregoing, there remains a need for oral dosage forms of apremilast that provide clinically desirable drug exposure.

SUMMARY

The disclosure provides oral dosage forms comprising a core tablet comprising (i) a drug layer comprising apremilast and hypromellose acetate succinate (HPMCAS) in an amorphous solid dispersion; and (ii) a swellable layer comprising one or more swellable polymers; and a coating layer disposed on the core tablet, wherein the oral dosage form surface comprises at least one drug release orifice.

The disclosure further provides oral dosage forms comprising a core tablet comprising (i) a drug layer comprising 8-11 wt % apremilast based upon total core tablet weight, 8-11 wt % hypromellose acetate succinate (HPMCAS) based upon total core tablet weight, 2-7 wt % mannitol based upon total core tablet weight, 40-45 wt % polyethylene oxide based upon total core tablet weight, 0.1-0.5 wt % magnesium stearate based upon total core tablet weight, and 0.1-0.5 wt % colloidal silicon dioxide based upon total core tablet weight, wherein the apremilast and HPMCAS are in a solid dispersion; (ii) a swellable layer comprising 18-25 wt % polyethylene oxide based upon total core tablet weight, 7-10 wt % microcrystalline cellulose based upon total core tablet weight, 1.5-3.5 wt. % sodium chloride based upon total core tablet weight, 0.01-0.2 wt % iron oxide based upon total core tablet weight, and 0.05-0.3 wt % magnesium stearate based upon total core tablet weight; and a coating layer disposed on the core tablet and comprising cellulose acetate and polyethylene glycol; wherein the oral dosage form surface comprising at least one drug release orifice.

The disclosure also provides oral dosage forms comprising a core tablet comprising (i) a drug layer comprising 10-15 wt. % apremilast based upon total core tablet weight, 10-15 wt % hypromellose acetate succinate (HPMCAS) based upon total core tablet weight, 30-40 wt % polyethylene oxide based upon total core tablet weight, 2-8 wt % sodium chloride based upon total core tablet weight, 0.1-0.5 wt % magnesium stearate based upon total core tablet weight, and 0.1-0.5 wt % colloidal silicon dioxide based upon total core tablet weight, wherein the apremilast and HPMCAS are in a solid dispersion; (ii) a swellable layer comprising 18-25 wt % polyethylene oxide based upon total core tablet weight, 7.5-10.0 wt % microcrystalline cellulose based upon total core tablet weight, 2-4 wt % sodium chloride based upon total core tablet weight, 0.01-0.1 wt % iron oxide based upon total core tablet weight, and 0.05-0.3 wt % magnesium stearate based upon total core tablet weight; and a coating layer disposed on the core tablet and comprising cellulose acetate and polyethylene glycol; wherein the oral dosage form surface comprising at least one drug release orifice.

DETAILED DESCRIPTION

Figure 1:
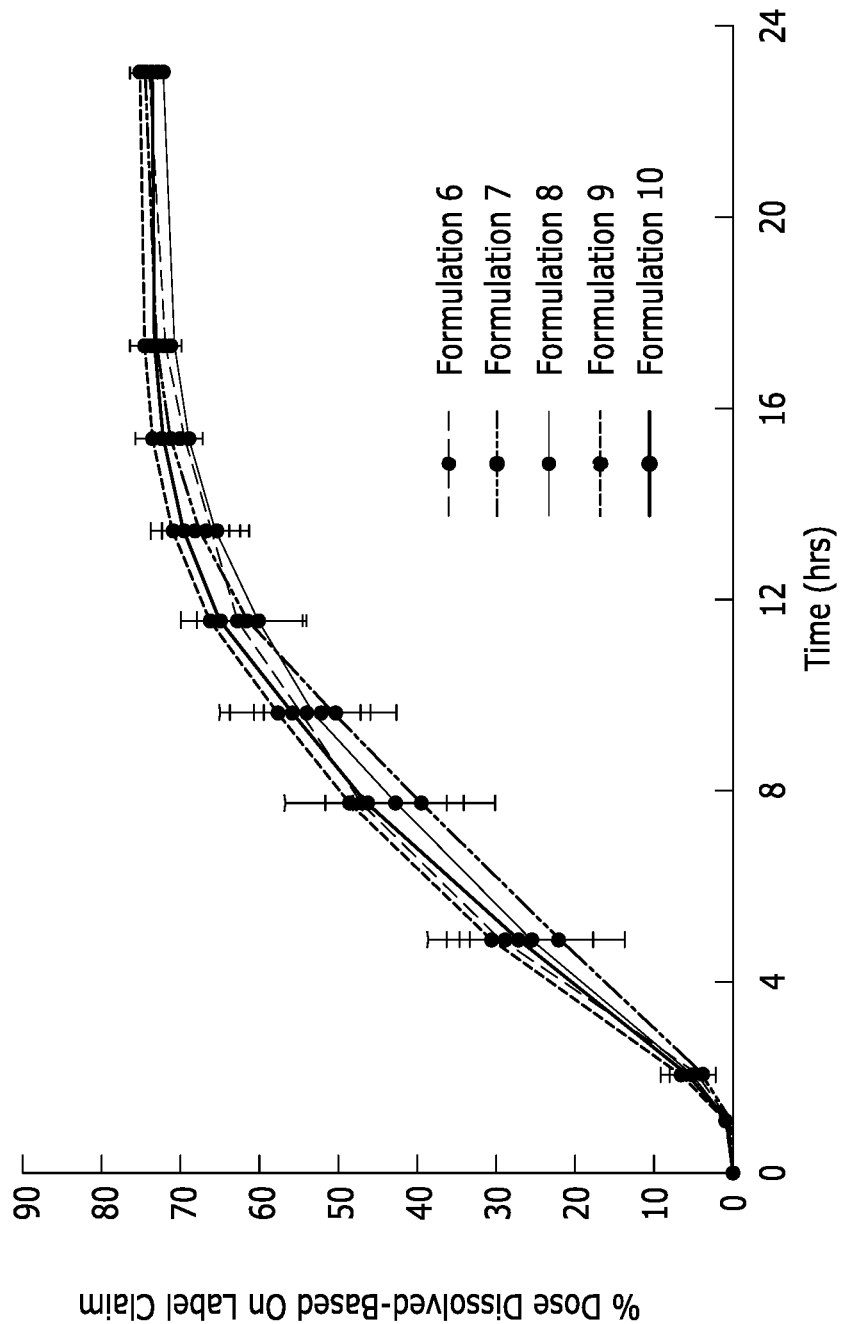
FIG. 1 shows dissolution profiles of Tablets 6-10.

Provided herein are oral dosage forms suitable for providing once-a-day (QD) dosing of apremilast. In some embodiments, the disclosed oral dosage forms are administered under fed conditions.

The oral dosage forms disclosed herein comprise a core tablet, a coating layer disposed on the core tablet, and at least one drug release orifice. In some embodiments, the oral dosage forms further comprise a sub-coat layer between the core tablet and the coating layer.

Core Tablet

The core tablet of the disclosed oral dosage forms comprises i) a drug layer comprising apremilast and hypromellose acetate succinate (HPMCAS) in an amorphous solid dispersion and ii) a swellable layer comprising one or more swellable polymers.

Drug Layer

The drug layer comprises a suitable amount of apremilast. Desirably, the drug layer contains an amount of apremilast that is suitable to provide once-a-day delivery/dosing of apremilast. If the oral dosage forms comprise too little apremilast, then the dosage forms will not deliver a clinically suitable amount of apremilast and will not be efficacious when dosed QD. Conversely, if the oral dosage forms comprise too much apremilast then the dosage forms are inefficient in their use of apremilast and overly costly. Moreover, if too much or too little apremilast is present then the bioequivalence of the dosage forms and/or the flux and release of apremilast from the dosage forms can be negatively impacted. In some embodiments, the apremilast is present in an amount of 6-15 wt % of the core tablet. Some examples of contemplated amounts of apremilast include, but are not limited to, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, and 16.0 wt % of the core tablet. In some embodiments, the apremilast is present in an amount of 8-11 wt % of the core tablet. In various embodiments, the apremilast is present in an amount of 9.6 wt % of the core tablet, 10.2 wt % of the core tablet, or 12.5 wt % of the core tablet.

In some embodiments, in conjunction with other above or below embodiments, the oral dosage forms comprise a total amount of 25-100 mg apremilast (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg apremilast). In some embodiments, in conjunction with other above or below embodiments, the oral dosage forms comprise 25-30 mg apremilast or 50-100 mg apremilast (e.g., 50-60 mg or 65-85 mg apremilast).

In various embodiments, in conjunction with other above or below embodiments, the oral dosage forms comprise 70, 75, or 80 mg apremilast. In some embodiments, the oral dosage forms comprises 27.5 mg apremilast, 55 mg of apremilast, 75 mg apremilast, or 100 mg apremilast.

In addition to apremilast, the drug layer also comprises HPMCAS. As used herein, HPMCAS refers to a family of cellulose derivatives that can have (1) two types of ether substituents, methyl and/or 2-hydroxypropyl and (2) two types of ester substituents, acetyl and/or succinyl. HPMCAS is also known by the chemical name 0-(2-hydroxypropyl)-O-methyl-cellulose acetate succinate. The degree of substitution for each of the four general types just noted can be varied over a wide range to affect the chemical and physical properties of the polymer. This versatility of HPMCAS allows its structure to be optimized to obtain good performance with a particular drug of interest. HPMCAS can be synthesized or purchased commercially. Three examples of commercially available HPMCAS include Shin-Etsu AQOAT®-LF, Shin-Etsu AQOAT®-MF, and Shin-Etsu AQOAT®-HF. All three of these polymers are manufactured by Shin-Etsu Chemical Co., Ltd. (Tokyo, Japan). In some embodiments, the HPMCAS is L grade (e.g., HPMCAS-LF or HPMCAS-LG or HPMCAS-LMP), wherein it is understood that L, M, and H grades of HPMCAS vary in acetyl and succinoyl contents. The L, M and H grades also refer to the pH at which the polymers dissolve (L=low pH>5.5, M=medium pH 6.0 and H=high pH 6.5). LF, LG and LMP grades refer to differing average particle size (F is cohesive fine powder—5 µm, MP is medium particle size—200 µm and G is free-flowing granules—1000 µm).

The HPMCAS has any suitable molecular weight. In some embodiments, the mean weight-average molecular weight range for HPMCAS is 10,000 to one million daltons (e.g., 10,000 to 400,000 daltons or 55,000 to 115,000 daltons, as determined using polyethylene oxide standards). Note that molecular weight can be presented herein as daltons (Da) or as g/mol, which are used interchangeably throughout. The molecular weight range can also vary based on the degree of substitution (e.g., amount of acetyl and/or succinyl groups present). For example, in various embodiments, in conjunction with other above or below embodiments, the mean weight-average molecular weight of the HPMCAS is approximately 15,000 to 20,000 daltons, for example, 15,000, 16,000, 17,000, 18,000, 19,000, or 20,000 daltons. In some embodiments, mean weight-average molecular weight of the HPMCAS is 17,700, 17,900, 18,800, 18,900, 20,400, or 21,200 daltons. In some embodiments, in conjunction with other above or below embodiments, the number-average molecular weight is approximately 13,000 daltons.

The drug layer comprises a suitable amount of HPMCAS. If the drug layer comprises too little or too much HPMCAS, then the amorphous solid dispersion may not have the desired release properties. In some embodiments, the HPMCAS is present in an amount of 6-15 wt % of the core tablet (e.g. 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 wt % of the core tablet). In some embodiments, the HPMCAS is present in an amount of 8-11 wt % of the core tablet. In various embodiments, the HPMCAS is present in an amount of 9.6 wt. % of the core tablet, 10.2 wt % of the core tablet, or 12.5 wt % of the core tablet.

In some embodiments, in conjunction with other above or below embodiments, the oral dosage forms comprise a total amount of 25-100 mg HPMCAS (e.g., 25, 26, 27, 28, 29, 30, 31, 32, 33, 34, 35, 36, 37, 38, 39, 40, 41, 42, 43, 44, 45,46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg HPMCAS). In some embodiments, in conjunction with other above or below embodiments, the oral dosage forms comprise 65-85 mg of HPMCAS. In various embodiments, in conjunction with other above or below embodiments, the oral dosage forms comprise 25-30 mg HPMCAS or 50-100 mg HPMCAS (e.g., 50-60 mg or 65-85 mg HPMCAS). In various embodiments, in conjunction with other above or below embodiments, the oral dosage forms comprise 70, 75, or 80 mg HPMCAS. In some embodiments, the oral dosage forms comprises 27.5 mg HPMCAS, 55 mg of HPMCAS, 75 mg HPMCAS, or 100 mg HPMCAS.

In various embodiments, the apremilast and HPMCAS are present in a weight ratio of 40:60 to 60:40 in the core tablet. For example, in some embodiments, the apremilast: HPMCAS weight ratio in the core tablet is: 40:60, 41:59, 42:58, 43:57, 44:56, 45:55, 46:56, 47:53, 48:52, 49:51, 50:50, 51:49, 52:48, 53:47, 54:46, 55:45, 56:44, 57:43, 58:42, 59:41, or 60:40. In some embodiments, the apremilast and HPMCAS are present in a weight ratio of 45:55 to 55:45 in the core tablet. In various embodiments, the apremilast and HPMCAS are present in a weight ratio of 48:52 to 52:48 in the core tablet. In some embodiments, the apremilast and HPMCAS are present in a weight ratio of 50:50 in the core tablet.

Amorphous Solid Dispersion

The apremilast and HPMCAS are present as an amorphous solid dispersion in the core tablet. Without wishing to be bound to any particular theory, it is believed that that the amorphous solid dispersion provides improved bioavailabilty of apremilast due to, for example, 1) improved drug dispersion, thereby preventing or retarding the rate of crystallization in the solid state, 2) improved dissolution in vivo, thereby allowing the drug to be released in the gastrointestinal tract, and 3) inhibiting the precipitation or crystallization of aqueous dissolved drug. Apremilast is required to be maintained amorphous in the composition disclosed herein, as it has been found that small amounts (e.g., 1.5 wt % or less) of crystalline apremilast can result in slower dissolution of the solid dispersion.

In some embodiments, in conjunction with other above or below embodiments, the amorphous solid dispersion is spray-dried. It has been found that a spray-dried solid dispersion (SDD) of apremilast in HPMCAS provide unexpectedly good solubility and improved ease of formulation. As is understood, spray-drying refers to processes involving breaking up liquid mixtures into small droplets (atomization) and rapidly removing solvent from the mixture in a container where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01-0.50 atm); (2) mixing the liquid droplets with a warm drying gas; or (3) both. For example, a solution of a drug and HPMCAS in acetone can be suitably spray-dried by spraying the solution at a temperature of 50° C. (the vapor pressure of acetone at 50° C. is about 0.8 atm) into a chamber held at 0.01-0.2 atm total pressure by connecting the outlet to a vacuum pump. Alternatively, the acetone solution can be sprayed into a chamber where it is mixed with nitrogen or other inert gas at a temperature of 80-180° C. and a pressure of 1.0-1.2 atm.

Generally, the temperature and flow rate of the drying gas is chosen so that the HPMCAS/drug-solution droplets are dry enough by the time they reach the wall of the apparatus that they are essentially solid, so that they form a fine powder and do not stick to the apparatus wall. The actual length of time to achieve this level of dryness depends on the size of the droplets. Droplet sizes generally range from 1 µm to 500 µm in diameter, with 5 to 100 µm being more typical. The large surface-to-volume ratio of the droplets and the large driving force for evaporation of solvent leads to actual drying times of a few seconds or less. This rapid drying is important to the particles maintaining a uniform, homogeneous composition instead of separating into drug-rich and polymer-rich phases. Such dispersions which have a homogeneous composition can be considered solid solutions and may be supersaturated in drug. Such homogeneous dispersions are preferred in that the maximum supersaturated concentration (MSSC) value obtained when a large amount of drug is dosed can be higher for such dispersions relative to dispersions for which at least a portion of the drug is present as a drug-rich amorphous or crystalline phase. Solidification times should be less than 20 seconds, preferably less than 5 seconds, and more preferably less than 2 seconds. In general, to achieve this rapid solidification of the drug/polymer solution, it is preferred that the size of droplets formed during the spray drying process are less than 100 µm in diameter, preferably less than 50 µm in diameter, and more preferably less than 25 µm in diameter. The resultant solid particles thus formed are generally less than 100 µm in diameter, preferably less than 50 µm in diameter, more preferably less than 25 µm in diameter.

Following solidification, the solid powder may stay in the spray-drying chamber for 5-50 seconds, further evaporating solvent from the solid powder. The final solvent content of the solid dispersion as it exits the dryer should be low, since this reduces the mobility of drug molecules in the dispersion, thereby improving its stability. Generally, the residual solvent content of the dispersion should be less than 10 wt % and preferably less than 2 wt %.

The dispersions can then be post-processed to prepare them for administration using methods known in the art such as roller compaction, fluid bed agglomeration, or spray coating. Spray-drying processes and spray-drying equipment are described generally in, for example, Chemical Engineers' Handbook, Sixth Edition (R. H. Perry, D. W. Green, J. O. Maloney, eds.) McGraw-Hill Book Co. 1984, page 20-54 to 20-57. More details on spray-drying processes and equipment are reviewed by Marshall ("Atomization and Spray-Drying," Chem. Eng. Prog. Monogr. Series, 50 [1954] 2).

In some embodiments, the solution spray-dried to form the HPMCAS/apremilast dispersion contains only apremilast and HPMCAS in a solvent. In some embodiments, the ratio of apremilast to HPMCAS in the solution is 0.2-1.2 to 1-100 or 0.4-1.2 to 1-20. In some embodiments, the ratio of apremilast to HPMCAS in the spray-drying solution is 1.2-0.8 to 1. Solvents suitable for spray-drying can be any organic compound in which the apremilast and HPMCAS are mutually soluble. Preferably, the solvent is also volatile with a boiling point of 150° C. or less. In some embodiments, the solvents include alcohols such as methanol, ethanol, n-propanol, iso-propanol, and butanol; ketones such as acetone, methyl ethyl ketone and methyl iso-butyl ketone; esters such as ethyl acetate and propyl acetate; and various other solvents such as acetonitrile, methylene chloride, toluene, and 1,1,1-trichloroethane. Lower volatility solvents such as dimethyl acetamide or dimethylsulfoxide can also be used. Mixtures of solvents can also be used, as can mixtures with water as long as the polymer and HPMCAS are sufficiently soluble to make the spray-drying process practical. In some embodiments, the solvent comprises acetone.

In some embodiments, spray-dried solutions and the resulting dispersions can also contain various excipients/additives that aid in the stability, dissolution, tableting, or processing of the dispersion, as described herein. In some embodiments, examples of such additives include: surfactants, pH-controlling substances (e.g., acids, bases, buffers), diluents/fillers, disintegrants, lubricants, or binders. Such excipients/additives, when present, can be added directly to the spray-drying solution such that the additive is dissolved or suspended in the solution as a slurry. Alternatively, such additives can be added following the spray-drying process to aid in forming the final dosage form.

Water Soluble Polymer

In some embodiments, the drug layer comprises a water soluble polymer. The water soluble polymer in the drug layer, when present, is any suitable water soluble polymer. Suitable water soluble polymers include, for example, polyethylene oxide, and a combination thereof. In various embodiments, the water soluble polymer is polyethylene oxide.

The water soluble polymer in the drug layer has a suitable molecular weight. For example, in embodiments wherein the water soluble polymer in the drug layer is polyethylene oxide (PEO), the polyethylene oxide has an average molecular weight of 200,000 Da or higher. In some embodiments, the polyethylene oxide has an average molecular weight of 200,000 Da to 300,000 Da (e.g., 200,000 and/or 300,000 Da), and/or 600,000 Da. It has been discovered that some embodiments exhibit improved stability wherein the drug layer comprises polyethylene oxide having more than one average molecular weight (e.g., a mixture of polyethylene oxides). For example, in embodiments wherein the drug layer comprises a mixture of polyethylene oxides of molecular weight of 200,000 Da and 300,000 Da, the amount of crystalline apremilast that forms during some stability studies (e.g., accelerated stability studies) is less than in embodiments comprising only one low molecular weight polyethylene oxide (e.g., molecular weight of 200,000 Da). In some cases, the polyethylene oxide is a mixture of 1 to 1 by weight 200 kDa PEO to 300 kDa PEO. In some cases, the polyethylene oxide is a mixture of 20:80 by weight 200 kDa PEO to 300 kDa PEO. In some cases, the polyethylene oxide is 300 kDa PEO. Certain embodiments comprising high molecular weight polyethylene oxides (e.g., molecular weight of at least 300,000 Da), and further comprising an osmotic agent (e.g., sodium chloride) in the drug layer, may provide improved dissolution, lag times (e.g., reduced lag time), and stability.

Illustrative polyethylene oxides suitable for the drug layer is the POLYOX WSR line of PEO commercially available from Dupont (Midland, MI), including POLYOX® WSR N80, POLYOX® WSR N750, and POLYOX® WSR 205. POLYOX® WSR N80 (commercially available from Dupont; Midland, MI) has the following physical properties: MW of 200,000 Da; viscosity of 65-115 cP; silicon dioxide content of 0.8-3.0 wt %; particle size through 10 mesh: 100 min; particle size through 20 mesh: 96-100 min; POLYOX® WSR N750 (commercially available from Dupont; Midland, MI) has the following physical properties: MW of 300,000 Da; viscosity of 600-1,200 cP; silicon dioxide content of 0.8-3.0 wt %; particle size through 10 mesh: 100 min; particle size through 20 mesh: 96-100 min; and POLYOX® WSR 205 (commercially available from Dupont; Midland, MI) has the following physical properties: MW of 600,000 Da; viscosity of 6800-8800 cP; and silicon dioxide content of 0.8-3.0 wt %.

The water soluble polymer is present in a suitable amount. For example, in some embodiments, the water soluble polymer is present in an amount of 30-55 wt % of the core tablet (e.g., 30, 31, 32, 33, 34, 35, 36, 37, 38, 39, 40, 41, 42, 43, 44, 45, 46, 47, 48, 49, 50, 51, 52, 53, 54, or 55 wt % of the core tablet). In some embodiments, the water soluble polymer is present in an amount of 30-55, 35-50, 35-45, 35-40, 40-55, 40-50, 45-55, or 45-50 wt % of the core tablet. In some embodiments, in conjunction with other above or below embodiments, the water soluble polymer (e.g., polyethylene oxide) is present in 34.3 wt % of the core tablet, 35 wt % of the core tablet, 37.6 wt % of the core tablet, or 42.7 wt % of the core tablet. In various embodiments, in conjunction with other above or below embodiments, the water soluble polymer and apremilast are present in a weight ratio of 2-6 to 1 in the drug layer. For example, in various embodiments the weight ratio of water soluble polymer to apremilast in the drug layer is 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 to 1. In some embodiments, in conjunction with other above or below embodiments, the weight ratio of water soluble polymer to apremilast in the drug layer is 2.7, 2.8, 3.0, 3.7, 4.2, or 5.1 to 1.

In some embodiments, the oral dosage forms comprise 100 mg or more polyethylene oxide in the drug layer, for example, 105, 110, 115, 120, or 125 mg polyethylene oxide in the drug layer. In some embodiments, the oral dosage forms comprise 200 mg or more polyethylene oxide in the drug layer, for example, 205, 210, 215, 220, 225, 230, 235, 240, 245, 250, 255, 260, 265, 270, 275, 280, 285, or 290 mg polyethylene oxide in the drug layer. In some embodiments, the oral dosage forms comprise 300 mg or more polyethylene oxide in the drug layer, for example, 305, 310, 315, 320, 325, 330, 335, 340, 345, 350, 355, or 360 mg polyethylene oxide in the drug layer. In some embodiments, in conjunction with other above or below embodiments, the oral dosage forms disclosed herein comprise 115.6 mg, 206 mg, 230.9 mg, 274.6 mg, 301.4 mg, 307.2 mg, 314.8 mg, 332.8 mg, or 358.4 mg polyethylene oxide in the drug layer.

Diluents, Lubricants, and Glidants

In some embodiments, in conjunction with other embodiments above or below, the drug layer comprises a diluent. The diluent can be extragranular (EG) and/or intragranular (IG). In some embodiments, the diluent is intragranular (IG). In some embodiments, the drug layer comprises intragranular and extragranular diluent. The diluent is present in any suitable amount. In some embodiments, in conjunction with other above or below embodiments, the diluent is present in amount of 2-7 wt % of the core tablet (e.g., 2, 2.5, 3.0, 3.5, 4.0, 4.5, 5.0, 5.5, 6.0, 6.5, or 7.0 wt % of the core tablet). In some embodiments, the diluent is present in 3.0 wt % of the core tablet or 4.8 wt. % of the core tablet.

Nonlimiting examples of diluents include lactose, sucrose, glucose, mannitol, sorbitol, calcium phosphate, calcium carbonate, microcrystalline cellulose and cellulose. An illustrative suitable diluent in the drug layer is mannitol. In embodiments, wherein the diluent comprises mannitol, the drug layer typically comprises 5-60 mg mannitol (e.g., 5, 10, 15, 20, 25, 30, 35, 40, 45, 50, 55, or 60 mg mannitol). For example, in various embodiments, in conjunction with other above or below embodiments, the drug layer comprises 8.1 mg, 16.2 mg, 22.1 mg, 25.0 mg, 48.0 mg, 52.0 mg, or 56.0 mg mannitol. In some embodiments, the drug layer comprises 12.3 mg mannitol (IG) and 9.8 mg mannitol (EG), 9.0 mg mannitol (IG) and 7.2 mg mannitol (EG), 4.5 mg mannitol (IG) and 3.6 mg mannitol (EG), or 25 mg mannitol (IG) and 25 mg mannitol (EG). In some embodiments, the drug layer comprises 50 mg mannitol (EG). In some embodiments comprising both IG mannitol and EG mannitol, 55-57% of the total mannitol present is intragranular and 43-45% of the total mannitol present is extragranular.

In some embodiments, in conjunction with other embodiments above or below, the drug layer comprises a lubricant. The lubricant can be extragranular (EG) and/or intragranular (IG). In some embodiments, the lubricant is intragranular (IG). In some embodiments, the drug layer comprises intragranular and extragranular lubricant. The lubricant is present in any suitable amount. In some embodiments, in conjunction with other above or below embodiments, example, the lubricant is present in amount of 0.05-0.50 wt % of the core tablet (e.g., 0.05, 0.10, 0.15, 0.2, 0.25, 0.30, 0.35, 0.40, 0.45, or 0.50 wt % of the core tablet). In some embodiments, in conjunction with other above or below embodiments, the lubricant (e.g., magnesium stearate) is present in amount of 0.25 wt %, 0.31 wt %, 0.33 wt %, or 0.37 wt % of the core tablet.

Examples of lubricants include magnesium stearate, talc, starch, and cellulose. An illustrative suitable lubricant is magnesium stearate. In embodiments, wherein the lubricant comprises magnesium stearate, the drug layer typically comprises 1-5 mg of magnesium stearate (e.g., 1.0, 1.5, 2.0, 2.5, 3.0. 3.5, 4.0, 4.5, or 5.0 mg magnesium stearate). For example, in various embodiments, in conjunction with other above or below embodiments, the drug layer comprises 1.0, 1.7, 2.0, 2.4, 2.5, 2.6, 2.7, or 2.8 mg magnesium stearate. In some embodiments, the drug layer comprises 0.5, 0.9, 1.0, 1.2, 1.3, or 1.4 mg magnesium stearate (IG) and 0.5, 1.0, 1.2, 1.3, or 1.4 mg magnesium stearate (EG).

In some embodiments, in conjunction with other embodiments above or below, the drug layer comprises a glidant. In some embodiments, the glidant is extragranular. The glidant is present in any suitable amount. In some embodiments, in conjunction with other above or below embodiments, example, the glidant is present in amount of 0.05-0.50 wt % of the core tablet (e.g., 0.05, 0.10, 0.15, 0.2, 0.25, 0.30, 0.35, 0.40, 0.45, or 0.50 wt % of the core tablet). In some embodiments, in conjunction with other above or below embodiments, the glidant (e.g., colloidal silicon dioxide) is present in amount of 0.25 wt %, 0.33 wt %, 0.34 wt %, or 0.37 wt % of the core tablet.

Examples of glidants include silica, magnesium stearate, and talc. An illustrative suitable glidant is silicon dioxide (e.g., colloidal silicon dioxide). In embodiments, wherein the glidant comprises silicon dioxide, the drug layer typically comprises 0.5-5 mg silicon dioxide (e.g., 0.5, 0.6, 0.7, 0.8, 0.9, 1.0, 1.5, 2.0, 2.5, 3.0. 3.5, 4.0, 4.5, or 5.0 mg silicon dioxide). For example, in various embodiments, in conjunction with other above or below embodiments, the drug layer comprises 0.9, 1.8, 2.0, 2.4, 2.5, 2.6, 2.7, or 2.8 mg silicon dioxide.

In some embodiments, the drug layer of the disclosed oral dosage forms further comprises an osmotic agent. When present, the osmotic agent of the drug layer can be any suitable osmotic agent. Nonlimiting examples of osmotic agents include sugars and sodium chloride. In some embodiments, in conjunction with other above or below embodiments, the osmotic agent of the drug layer comprises sodium chloride. The osmotic agent of the drug layer is present in any suitable amount. In some embodiments, in conjunction with other above or below embodiments, the drug layer comprises 2-12 wt % osmotic agent (e.g., 2, 3, 4, 5, 6, 7, 8, 9, 10, 11, or 12 wt % osmotic agent). In some embodiments, the drug layer comprises 5 wt %, 7.7 wt %, or 10 wt % osmotic agent (e.g., sodium chloride). Depending on the dosage strength of the dosage form, the drug layer comprises 15-60 mg osmotic agent (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mg osmotic agent). In some embodiments, the drug layer comprises 18.0, 26.7, 40, or 53.3 osmotic agent (e.g., sodium chloride). In some embodiments, the osmotic agent (e.g., sodium chloride) of the drug layer is present in an amount of 3-8 wt % of the core tablet (e.g., 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0 wt % of the core tablet). In some embodiments, the osmotic agent (e.g., sodium chloride) of the drug layer is present in an amount of 3.3 wt %, 5.1 wt %, or 6.7 wt % of the core tablet.

Swellable Layer

The swellable layer comprises one or more swellable polymers. As such, the swellable layer expands when in contact with water, the expansion of which creates pressure which results in drug release from the drug layer through the at least one drug release orifice of the dosage form. In some embodiments, in conjunction with other above or below embodiments, the drug layers and swellable layers are present in a weight ratio of 2:1 in the core tablet.

The swellable polymer can be any suitable swellable polymer. In some embodiments, the swellable polymer comprises polyethylene oxide. An illustrative suitable polyethylene oxide for the swellable layer is, for example, POLYOX® WSR Coagulant (commercially available from Dupont; Midland, MI) having the following physical properties: MW of 5,000,000 Da; viscosity: 5500-7500 cP; and silicon dioxide 0.8-3.0 wt %. The polyethylene oxide of the swellable layer typically has a higher molecular weight than polyethylene oxide of the drug layer (e.g., 5,000,000 Da).

The swellable polymer is present in any suitable amount. Typically, the swellable polymer is present in an amount of 50-70 wt % of the swellable layer (e.g., polyethylene oxide) (e.g., 50, 51, 52, 53, 54, 55, 56, 57, 58, 59, 60, 61, 62, 63, 64, 65, 66, 67, 68, 69, or 70 wt % of the swellable layer). In some embodiments, in conjunction with other above or below embodiments, the swellable polymer is present in an amount of 50-70 wt %, 55-70 wt %, or 55-65 wt % of the swellable layer. In some embodiments, the swellable polymer is present in 64.8 wt %, 64.9 wt %, or 65 wt % of the swellable layer. Depending on the dosage strength of the dosage form, the swellable polymer is present in an amount of 50-75 mg, 100-130 mg, 150-200 mg in the swellable layer. In some embodiments, the swellable polymer (e.g., polyethylene oxide) is present in an amount of 58.6 mg, 117.0 mg, 129.8 mg, 159.6 mg, or 173.1 mg in the swellable layer. In some embodiments, the swellable polymer (e.g., polyethylene oxide) is present in an amount of 15-25 wt % of the core tablet (e.g., 15, 16, 17, 18, 19, 20, 21, 22, 23, 24, or 25 wt % of the core tablet). In some embodiments, the swellable polymer comprises 21.6 wt % or 22 wt % of the core tablet.

In some embodiments, the swellable layer further comprises one or more of an osmotic agent, a diluent, a lubricant, and a colorant.

The osmotic agent of the swellable layer can be any suitable osmotic agent as described herein. Nonlimiting examples of osmotic agents include sugars and sodium chloride. In some embodiments, in conjunction with other above or below embodiments, the osmotic agent comprises sodium chloride. The osmotic agent is present in any suitable amount. In some embodiments, in conjunction with other above or below embodiments, the swellable layer comprises 5-15 wt % osmotic agent (e.g., 5, 6, 7, 8, 9, 10, 11, 12, 13, 14, or 15 wt % osmotic agent). In some embodiments, the swellable layer comprises 5-10 wt %, 5-7 wt %, 8-12 wt %, or 8-10 wt % osmotic agent. In some embodiments, the swellable layer comprises 8.4 wt %, 8.5 wt %, 8.6 wt %, 9.1 wt %, or 9.8 wt % osmotic agent. Depending on the dosage strength of the dosage form, the swellable layer comprises 5-25 mg osmotic agent (e.g., 5, 6, 7, 8, 9, 10, 11, 12, 13, 14, 15, 16, 17, 18, 19, 20, 21, 22, 23, 24, or 25 mg osmotic agent). In some embodiments, the swellable layer comprises 7.8 mg, 15.5 mg, 17.2 mg, 20.6 mg, 21.1 mg, 22.4 mg, 22.9 mg, or 24.1 mg osmotic agent (e.g., sodium chloride). In some embodiments, the osmotic agent (e.g., sodium chloride) is present in an amount of 1.5-3.5 wt % of the total core tablet (e.g., 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5 wt % of the core tablet). In some embodiments, the osmotic agent (e.g. sodium chloride) is present in an amount of 2.80, 2.85, 2.90, or 2.95 wt % of the core tablet.

The diluent of the swellable layer can be any suitable diluent as described herein. An illustrative suitable diluent in the swellable layer is microcrystalline cellulose. In some embodiments, in conjunction with other above or below embodiments, the diluent comprises microcrystalline cellulose. The diluent is present in any suitable amount. In some embodiments, the diluent (e.g., microcrystalline cellulose) is present in an amount of 20-35 wt % of the swellable layer (e.g., 20, 21, 22, 23, 24, 25, 26, 27, 28, 29, 30, 31, 32, 33, 34, or 35 wt %). In some embodiments, the diluent is present in an amount of 25.2 wt %, 25.8 wt %, 27.3 wt %, or 29.4 wt % of the swellable layer. In some embodiments, the diluent is present in an amount of 7-10 wt % of the core tablet (e.g., 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 wt % of the core tablet).

The lubricant of the swellable layer can be any suitable lubricant as described herein. An illustrative suitable lubricant in the swellable layer is magnesium stearate. The lubricant is present in any suitable amount. In some embodiments, the lubricant is present in an amount of 0.3-1 wt % of the swellable layer (e.g., 0.3, 0.4, 0.5, 0.6, 0.7, 0.8, 0.9, 1.0 wt % of the swellable layer). In some embodiments, in conjunction with other above or below embodiments, the lubricant is present in an amount of 0.5 wt % or 0.6 wt % of the swellable layer. In some embodiments, in conjunction with other above or below embodiments, example, the lubricant of the swellable layer is present in amount of 0.05-0.50 wt % of the core tablet (e.g., 0.05, 0.10, 0.15, 0.2, 0.25, 0.30, 0.35, 0.40, 0.45, or 0.50 wt % of the core tablet). Depending on the dosage strength of the dosage form, in various embodiments, the swellable layer comprises 0.5, 0.9, 1.0, 1.1, 1.2, 1.3, 1.4, or 1.5 mg magnesium stearate.

The coloring agent can be any suitable coloring agent. An illustrative suitable coloring agent is iron oxide red. The coloring agent is present in any suitable amount. In some embodiments, in conjunction with other above or below embodiments, example, the coloring agent (e.g., iron oxide red) of the swellable layer is present in amount of 0.05-0.50 wt % of the core tablet (e.g., 0.05, 0.10, 0.15, 0.2, 0.25, 0.30, 0.35, 0.40, 0.45, or 0.50 wt % of the core tablet). In some embodiments, the coloring agent is present in an amount of 0.05, 0.06, 0.07, 0.08, 0.09, or 0.10 wt % of the core tablet. In various embodiments, in conjunction with other above or below embodiments, the swellable layer comprises 0.2 mg, 0.4 mg, or 0.5 mg coloring agent (e.g., iron oxide red).

Coating Layer

The oral dosage forms disclosed herein comprise a coating layer disposed on the core tablet. In some embodiments, the coating layer is present in an amount of 6.5-8.5 wt % based upon the total oral dosage form weight. In some embodiments, the coating layer is present in an amount of 7.5 wt % based upon the total oral dosage form weight. In some embodiments, the coating layer comprises cellulose acetate (CA) and polyethylene glycol (PEG). In various embodiments, the PEG has an average molecular weight of 3,000-4,000 Da, for example, 3,000-3,700 Da, or 3,350 Da.

The cellulose acetate and PEG are present in any suitable amounts. In some embodiments, the coating layer comprises 10-80 mg of CA (e.g., 10, 20, 25, 30, 35, 40, 45, 50, 55, 60, 65, 70, 75, or 80 mg CA). In some embodiments, the coating layer comprises 15.2, 30.3, 36.3, 37.4, 40.3, 41.3, 49.6, 72.0, and 74.9 mg CA.

In some embodiments, in conjunction with other above or below embodiments, the coating layer comprises 3.8, 7.6, 9.1, 9.4, 10.1, 10.3, 12.4, 18.0, or 18.7 mg PEG. In some embodiments, the CA and PEG are present in a CA:PEG weight ratio of 3.5 to 4.5:1. For example, in some embodiments, the weight ratio of CA to PEG in the coating layer is 3.5, 3.6, 3.7, 3.8, 3.9, 4.0, 4.1, 4.2, 4.3, 4.4, or 4.5. In some embodiments, the CA and PEG are present in a CA:PEG weight ratio of 4:1.

Sub-Coat Layer

In some embodiments, the disclosed oral dosage forms further comprise a sub-coat layer between the core tablet and coating layer. In some embodiments, the sub-coat layer comprises hydroxypropyl methylcellulose (HPMC).

The sub-coat layer, when present, is present in any suitable amount. In some embodiments, the sub-coat layer is present in an amount of 2-4 wt % of the oral dosage form (e.g., 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 wt % of the oral dosage form). In some embodiments, the sub-coat layer is present in an amount of 2.3 wt % of the oral dosage form. In some embodiments, the sub-coat layer is present in an amount of 3.4 wt % of the oral dosage form.

In some embodiments, the coating layer further comprises a color coat layer. The color coat layer comprises one or more suitable colorants. An illustrative suitable colorant is the Opadry® II colorants commercially available from Colorcon, Inc. (Harleysville, PA). The color coat layer is present in a suitable amount. In some embodiments, the color coat layer is present in an amount of 3-5 wt % (3.0, 3.5, 4.0, 4.5, 5.0 wt %) of the oral dosage form. In some embodiments, the color coat layer is present in an amount of 3.4 wt % of the oral dosage form.

Drug Release Orifice

The oral dosage forms disclosed herein comprise at least one drug release orifice. In some embodiments, the drug release orifice in made by drilling the oral dosage form. Typically, the drug release orifice ranges in size from 600 μm to 1.5 mm. In some embodiments, the oral dosage forms are drilled using a 900 μm drill. In some embodiments, the oral dosage forms are drilled using a 1600 μm drill. In some embodiments, the drug release orifice has a size of 1.2 mm.

In some embodiments, the disclosure provides oral dosage forms comprising a core tablet comprising (i) a drug layer comprising 8-11 wt % apremilast based upon total core tablet weight, 8-11 wt % hypromellose acetate succinate (HPMCAS) based upon total core tablet weight, 2-7 wt % mannitol based upon total core tablet weight, 40-45 wt % polyethylene oxide based upon total core tablet weight, 0.1-0.5 wt % magnesium stearate based upon total core tablet weight, and 0.1-0.5 wt % colloidal silicon dioxide based upon total core tablet weight, wherein the apremilast and HPMCAS are in a solid dispersion; (ii) a swellable layer comprising 18-25 wt % polyethylene oxide based upon total core tablet weight, 7-10 wt % microcrystalline cellulose based upon total core tablet weight, 1.5-3.5 wt. % sodium chloride based upon total core tablet weight, 0.01-0.2 wt % iron oxide based upon total core tablet weight, and 0.05-0.3 wt % magnesium stearate based upon total core tablet weight; and a coating layer disposed on the core tablet and comprising cellulose acetate and polyethylene glycol; wherein the oral dosage form surface comprising at least one drug release orifice.

In some embodiments, the disclosure provides oral dosage forms comprising a core tablet comprising a core tablet comprising (i) a drug layer comprising 75 mg apremilast, 75 mg hypromellose acetate succinate (HPMCAS), 22.1 mg mannitol, 314.8 mg polyethylene oxide, 2.4 mg magnesium stearate, and 2.5 mg colloidal silicon dioxide, wherein the apremilast and HPMCAS are in a solid dispersion; (ii) a swellable layer comprising 159.6 mg polyethylene oxide, 63.4 mg microcrystalline cellulose, 21.1 mg sodium chloride, 0.5 mg iron oxide, and 1.2 mg magnesium stearate; and a coating layer disposed on the core tablet and comprising cellulose acetate and polyethylene glycol; wherein the oral dosage form surface comprising at least one drug release orifice.

In some embodiments, the disclosure provides oral dosage forms comprising a core tablet comprising a core tablet comprising (i) a drug layer comprising 55 mg apremilast, 55 mg hypromellose acetate succinate (HPMCAS), 16.2 mg mannitol, 230.9 mg polyethylene oxide, 1.7 mg magnesium stearate, and 1.8 mg colloidal silicon dioxide, wherein the apremilast and HPMCAS are in a solid dispersion; (ii) a swellable layer comprising 117 mg polyethylene oxide, 46.5 mg microcrystalline cellulose, 15.5 mg sodium chloride, 0.4 mg iron oxide, and 0.9 mg magnesium stearate; and a coating layer disposed on the core tablet and comprising cellulose acetate and polyethylene glycol; wherein the oral dosage form surface comprising at least one drug release orifice.

In some embodiments, the disclosure provides oral dosage forms comprising a core tablet comprising a core tablet comprising (i) a drug layer comprising 27.5 mg apremilast, 27.5 mg hypromellose acetate succinate (HPMCAS), 8.1 mg mannitol, 115.6 mg polyethylene oxide, 1.0 mg magnesium stearate, and 0.9 mg colloidal silicon dioxide, wherein the apremilast and HPMCAS are in a solid dispersion; (ii) a swellable layer comprising 58.6 mg polyethylene oxide, 23.3 mg microcrystalline cellulose, 7.8 mg sodium chloride, 0.2 mg iron oxide, and 0.5 mg magnesium stearate; and a coating layer disposed on the core tablet and comprising cellulose acetate and polyethylene glycol; wherein the oral dosage form surface comprising at least one drug release orifice.

In some embodiments, the disclosure provides oral dosage forms comprising a core tablet comprising (i) a drug layer comprising 10-15 wt. % apremilast based upon total core tablet weight, 10-15 wt % hypromellose acetate succinate (HPMCAS) based upon total core tablet weight, 30-40 wt % polyethylene oxide based upon total core tablet weight, 2-8 wt % sodium chloride based upon total core tablet weight, 0.1-0.5 wt % magnesium stearate based upon total core tablet weight, and 0.1-0.5 wt % colloidal silicon dioxide based upon total core tablet weight, wherein the apremilast and HPMCAS are in a solid dispersion; and (ii) a swellable layer comprising 18-25 wt % polyethylene oxide based upon total core tablet weight, 7.5-10.0 wt % microcrystalline cellulose based upon total core tablet weight, 2-4 wt % sodium chloride based upon total core tablet weight, 0.01-0.1 wt % iron oxide based upon total core tablet weight, and 0.05-0.3 wt % magnesium stearate based upon total core tablet weight; and a coating layer disposed on the core tablet and comprising cellulose acetate and polyethylene glycol; wherein the oral dosage form surface comprising at least one drug release orifice.

In some embodiments, the disclosure provides oral dosage forms comprising a core tablet comprising a core tablet comprising (i) a drug layer comprising 100 mg apremilast, 100 mg hypromellose acetate succinate (HPMCAS), 301.4 mg polyethylene oxide, 26.7 mg sodium chloride, 2.6 mg magnesium stearate, and 2.7 mg colloidal silicon dioxide, wherein the apremilast and HPMCAS are in a solid dispersion; (ii) a swellable layer comprising 173.1 mg polyethylene oxide, 68.8 mg microcrystalline cellulose, 22.9 mg sodium chloride, 0.5 mg iron oxide, and 1.3 mg magnesium stearate; and a coating layer disposed on the core tablet and comprising cellulose acetate and polyethylene glycol; wherein the oral dosage form surface comprising at least one drug release orifice.

In some embodiments, the disclosure provides oral dosage forms comprising a core tablet comprising a core tablet comprising (i) a drug layer comprising 100 mg apremilast, 100 mg hypromellose acetate succinate (HPMCAS), 274.6 mg polyethylene oxide, 53.3 sodium chloride, 2.6 mg magnesium stearate, and 2.7 mg colloidal silicon dioxide, wherein the apremilast and HPMCAS are in a solid dispersion; (ii) a swellable layer comprising 173.1 mg polyethylene oxide, 68.8 mg microcrystalline cellulose, 22.9 mg sodium chloride, 0.5 mg iron oxide, and 1.3 mg magnesium stearate; and a coating layer disposed on the core tablet and comprising cellulose acetate and polyethylene glycol; wherein the oral dosage form surface comprising at least one drug release orifice.

In some embodiments, the disclosure provides an oral dosage form comprising a) a core table comprising (i) a drug layer comprising 60 mg apremilast, 60 mg hypromellose acetate succinate (HPMCAS), 48 mg mannitol, 307.2 mg polyethylene oxide, 2.4 mg magnesium stearate, and 2.4 mg colloidal silicon dioxide, wherein the apremilast and HPMCAS are in a solid dispersion; and (ii) a swellable layer comprising 155.8 mg polyethylene oxide, 61.9 mg microcrystalline cellulose, 20.6 mg sodium chloride, 0.5 mg iron oxide, and 1.2 mg magnesium stearate; and b) a coating layer comprising 37.4 mg CA and 9.4 mg PEG, wherein the oral drug dosage form comprises at least one drug release orifice as described herein.

In some embodiments, the disclosure provides an oral dosage form comprising a) a core table comprising (i) a drug layer comprising 60 mg apremilast, 60 mg hypromellose acetate succinate (HPMCAS), 48 mg mannitol, 307.2 mg polyethylene oxide, 2.4 mg magnesium stearate, and 2.4 mg colloidal silicon dioxide, wherein the apremilast and HPMCAS are in a solid dispersion; (ii) a swellable layer comprising 155.8 mg polyethylene oxide, 61.9 mg microcrystalline cellulose, 20.6 mg sodium chloride, 0.5 mg iron oxide, and 1.2 mg magnesium stearate; and b) a coating layer comprising 72.0 mg CA and 18.0 mg PEG, wherein the oral drug dosage form comprises at least one drug release orifice as described herein.

In some embodiments, the disclosure provides an oral dosage form comprising a) a core table comprising (i) a drug layer comprising 65 mg apremilast, 65 mg hypromellose acetate succinate (HPMCAS), 52 mg mannitol, 332.8 mg polyethylene oxide, 2.6 mg magnesium stearate, and 2.6 mg colloidal silicon dioxide, wherein the apremilast and HPMCAS are in a solid dispersion; (ii) a swellable layer comprising 168.7 mg polyethylene oxide, 67.1 mg microcrystalline cellulose, 22.4 mg sodium chloride, 0.5 mg iron oxide, and 1.3 mg magnesium stearate; and b) a coating layer comprising 37.4 mg CA and 9.4 mg PEG, wherein the oral drug dosage form comprises at least one drug release orifice as described herein.

In some embodiments, the disclosure provides an oral dosage form comprising a) a core table comprising (i) a drug layer comprising 65 mg apremilast, 65 mg hypromellose acetate succinate (HPMCAS), 52 mg mannitol, 332.8 mg polyethylene oxide, 2.6 mg magnesium stearate, and 2.6 mg colloidal silicon dioxide, wherein the apremilast and HPMCAS are in a solid dispersion; (ii) a swellable layer comprising 168.7 mg of polyethylene oxide, 67.1 mg microcrystalline cellulose, 22.4 mg sodium chloride, 0.5 mg iron oxide, and 1.3 mg magnesium stearate; and b) a coating layer comprising 74.9 mg CA and 18.7 mg PEG, wherein the oral drug dosage form comprises at least one drug release orifice as described herein.

In some embodiments, the disclosure provides an oral dosage form comprising a) a core table comprising (i) a drug layer comprising 70 mg apremilast, 70 mg hypromellose acetate succinate (HPMCAS), 56 mg mannitol, 358.4 mg polyethylene oxide, 2.8 mg magnesium stearate, and 2.8 mg colloidal silicon dioxide, wherein the apremilast and HPMCAS are in a solid dispersion; (ii) a swellable layer comprising 181.7 mg polyethylene oxide, 72.3 mg microcrystalline cellulose, 24.1 mg sodium chloride, 0.5 mg iron oxide, and 1.4 mg magnesium stearate; and b) a coating layer comprising 40.3 mg CA and 10.1 mg PEG, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 22.1 mg mannitol, 314.8 mg polyethylene oxide, 2.4 mg magnesium stearate, and 2.5 mg colloidal silicon dioxide, wherein the apremilast and HPMCAS are in a solid dispersion; (ii) a swellable layer comprising 159.6 mg polyethylene oxide, 63.4 mg microcrystalline cellulose, 21.1 mg sodium chloride, 0.5 mg iron oxide, and 1.2 mg magnesium stearate; b) a subcoat layer comprising 18.4 mg HPMC; and c) a coating layer comprising 36.3 mg CA and 9.1 mg PEG, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 22.1 mg mannitol, 314.8 mg polyethylene oxide, 2.4 mg magnesium stearate, and 2.5 mg colloidal silicon dioxide, wherein the apremilast and HPMCAS are in a solid dispersion; (ii) a swellable layer comprising 159.6 mg polyethylene oxide, 63.4 mg microcrystalline cellulose, 21.1 mg sodium chloride, 0.5 mg iron oxide, and 1.2 mg magnesium stearate; b) a subcoat layer comprising 18.4 mg HPMC; and c) a coating layer comprising 49.6 mg CA and 12.4 mg PEG, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 22.1 mg mannitol, 314.8 mg polyethylene oxide, 2.4 mg magnesium stearate, and 2.5 mg colloidal silicon dioxide, wherein the apremilast and HPMCAS are in a solid dispersion; (ii) a swellable layer comprising 159.6 mg polyethylene oxide, 63.4 mg microcrystalline cellulose, 21.1 mg sodium chloride, 0.5 mg iron oxide, and 1.2 mg magnesium stearate; b) a coating layer comprising 41.3 mg CA and 10.3 mg PEG, wherein the coating layer further comprises 27.6 mg of a colorant, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 22.1 mg mannitol, 314.8 mg polyethylene oxide, 2.4 mg magnesium stearate, and 2.5 mg colloidal silicon dioxide, wherein the apremilast and HPMCAS are in a solid dispersion; (ii) a swellable layer comprising 159.6 mg polyethylene oxide, 63.4 mg microcrystalline cellulose, 21.1 mg sodium chloride, 0.5 mg iron oxide, and 1.2 mg magnesium stearate; and b) a coating layer comprising 41.3 mg CA and 10.3 mg PEG, wherein coating layer further comprises 27.6 mg of colorant and the oral drug dosage form comprises at least one drug release orifice as described herein.

In some embodiments, the disclosure provides an oral dosage form comprising a) a core table comprising (i) a drug layer comprising 55 mg apremilast, 55 mg hypromellose acetate succinate (HPMCAS), 16.2 mg mannitol, 230.9 mg polyethylene oxide, 1.7 mg magnesium stearate, and 1.8 mg colloidal silicon dioxide, wherein the apremilast and HPMCAS are in a solid dispersion; (ii) a swellable layer comprising 117 mg polyethylene oxide, 46.5 mg microcrystalline cellulose, 15.5 mg sodium chloride, 0.4 mg iron oxide, and 0.9 mg magnesium stearate; and b) a coating layer comprising 30.3 mg CA and 7.6 mg PEG, wherein coating layer further comprises 20.2 mg of colorant and the oral drug dosage form comprises at least one drug release orifice as described herein.

In some embodiments, the disclosure provides an oral dosage form comprising a) a core table comprising (i) a drug layer comprising 27.5 mg apremilast, 27.5 mg hypromellose acetate succinate (HPMCAS), 8.1 mg mannitol, 115.6 mg polyethylene oxide, 1 mg magnesium stearate, and 0.9 mg colloidal silicon dioxide, wherein the apremilast and HPMCAS are in a solid dispersion; (ii) a swellable layer comprising 58.6 mg polyethylene oxide, 23.3 mg microcrystalline cellulose, 7.8 mg sodium chloride, 0.2 mg iron oxide, and 0.5 mg magnesium stearate; and b) a coating layer comprising 15.2 mg CA and 3.8 mg PEG, wherein coating layer further comprises 10.1 mg of colorant and the oral drug dosage form comprises at least one drug release orifice as described herein.

In some embodiments, the disclosure provides an oral dosage form comprising a) a core table comprising (i) a drug layer comprising 100 mg apremilast, 100 mg hypromellose acetate succinate (HPMCAS), 26.7 mg sodium chloride, 150.7 mg polyethylene oxide having a MW of 300,000 Da, 150.7 mg polyethylene oxide having a MW of 200,000, 2.6 mg magnesium stearate, and 2.7 mg colloidal silicon dioxide, wherein the apremilast and HPMCAS are in a solid dispersion; (ii) a swellable layer comprising 173.1 mg polyethylene oxide, 68.8 mg microcrystalline cellulose, 22.9 mg sodium chloride, 0.5 mg iron oxide, and 1.3 mg magnesium stearate; and b) a coating layer as described herein, wherein the oral drug dosage form comprises at least one drug release orifice as described herein.

In some embodiments, the disclosure provides an oral dosage form comprising a) a core table comprising (i) a drug layer comprising 100 mg apremilast, 100 mg hypromellose acetate succinate (HPMCAS), 53.3 mg sodium chloride, 274.6 mg polyethylene oxide having a MW of 300,000 Da, 2.6 mg magnesium stearate, and 2.7 mg colloidal silicon dioxide, wherein the apremilast and HPMCAS are in a solid dispersion; (ii) a swellable layer comprising 173.1 mg polyethylene oxide, 68.8 mg microcrystalline cellulose, 22.9 mg sodium chloride, 0.5 mg iron oxide, and 1.3 mg magnesium stearate; and b) a coating layer as described herein, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 40 mg sodium chloride, 206 mg polyethylene oxide having a MW of 300,000 Da, 2 mg magnesium stearate, and 2 mg colloidal silicon dioxide, wherein the apremilast and HPMCAS are in a solid dispersion; (ii) a swellable layer comprising 129.8 mg polyethylene oxide, 51.6 mg microcrystalline cellulose, 17.2 mg sodium chloride, 0.4 mg iron oxide, and 1 mg magnesium stearate; and b) a coating layer as described herein, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 40 mg sodium chloride, 274.6 mg polyethylene oxide having a MW of 300,000 Da, 2 mg magnesium stearate, 50 mg mannitol, and 2 mg colloidal silicon dioxide, wherein the apremilast and HPMCAS are in a solid dispersion; (ii) a swellable layer comprising 173.1 mg polyethylene oxide, 68.8 mg microcrystalline cellulose, 22.9 mg sodium chloride, 0.5 mg iron oxide, and 1.3 mg magnesium stearate; and b) a coating layer as described herein, wherein the oral drug dosage form comprises at least one drug release orifice as described herein.

In some embodiments, the disclosure provides an oral dosage form comprising a) a core table comprising (i) a drug layer comprising 75 mg apremilast, 75 mg hypromellose acetate succinate (HPMCAS), 40 mg sodium chloride, 274.6 mg polyethylene oxide having a MW of 300,000 Da, 2 mg magnesium stearate, 25 mg mannitol (IG), 25 mg mannitol (EG), and 2 mg colloidal silicon dioxide, wherein the apremilast and HPMCAS are in a solid dispersion; (ii) a swellable layer comprising 173.1 mg polyethylene oxide, 68.8 mg microcrystalline cellulose, 22.9 mg sodium chloride, 0.5 mg iron oxide, and 1.3 mg magnesium stearate; and b) a coating layer as described herein, wherein the oral drug dosage form comprises at least one drug release orifice as described herein.

Methods of Treating

The disclosure provides methods of treating a patient suffering from a disease or disorder ameliorated by inhibiting PDE4 comprising administering to the patient under fed conditions the oral dosage forms disclosed herein.

A subject in a fed state refers to a subject who has taken food or has had a meal. In some embodiments, the formulation disclosed herein is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In some cases, a formulation as disclosed herein is administered to a subject in a fed state 30 minutes post-meal. In various cases, a formulation as disclosed herein is administered to a subject in a fed state 1 hour post-meal. In some embodiments, a formulation as disclosed herein is administered to a subject with food.

In some embodiments, the disease or disorder is asthma, arthritis, psoriasis, inflammation, chronic or acute obstructive pulmonary diseases, chronic or acute pulmonary inflammatory diseases, cutaneous lupus erythematosis, inflammatory bowel disease, Crohn's Disease, Behcet's Disease, hidradenitis suppurativa, or colitis. In some embodiments, the disease or disorder arthritis. In some embodiments, the arthritis is psoriatic arthritis. In some embodiments, the disease or disorder is psoriasis. In some embodiments, the disease or disorder is colitis. In some embodiments, the colitis is ulcerative colitis. In some embodiments, the disease or disorder is Behcet's disease. In some embodiments, the disease or disorder is inflammatory bowel disease. In some embodiments, the disease or disorder is hidradenitis suppurativa.

In some embodiments, the disclosed oral dosage forms are administered after an initial titration with a conventional twice-a-day apremilast formulation.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; (iv) 20 mg in the morning and 20 mg after noon on the fourth day of administration; (v) 20 mg in the morning and 30 mg after noon on the fifth day of administration; and (vi) 30 mg in the morning and 30 mg after noon on days 6-14 of administration; and the disclosed oral dosage form once daily every subsequent day of administration. In some embodiments, the oral dosage form administered on day 15 and thereafter comprises 27.5 mg apremilast, 55 mg apremilast, or 75 mg apremilast.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; (iv) 20 mg in the morning and 20 mg after noon on the fourth day of administration; (v) 20 mg in the morning and 30 mg after noon on the fifth day of administration; and (vi) 30 mg in the morning and 30 mg after noon on Days 6-14 of administration; and a disclosed oral dosage form having 75 mg apremilast once daily in the morning Day 15 and every subsequent day of administration.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; (iv) 20 mg in the morning and 20 mg after noon on the fourth day of administration; (v) 20 mg in the morning and 30 mg after noon on the fifth day of administration; and (vi) an oral dosage form as disclosed herein having 75 mg apremilast once daily in the morning Day 6 and thereafter.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; and (iv) an oral dosage form as disclosed herein having 55 mg apremilast once daily in the morning Day 4 and thereafter.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; (iv) 20 mg in the morning and 20 mg after noon on Day 4 to Day 14; and (v) an oral dosage form as disclosed herein having 55 mg apremilast once daily in the morning Day 15 and thereafter.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; and (iv) two oral dosage forms as disclosed herein having 27.5 mg apremilast (for a total of 55 mg apremilast) once daily in the morning Day 4 and thereafter.

In some embodiments, the disclosed method comprises the following initial titration schedule: (i) 10 mg in the morning on the first day of administration; (ii) 10 mg in the morning and 10 mg after noon on the second day of administration; (iii) 10 mg in the morning and 20 mg after noon on the third day of administration; (iv) 20 mg in the morning and 20 mg after noon on Day 4 to Day 14; and (v) two oral dosage forms as disclosed herein having 27.5 mg apremilast (for a total of 55 mg apremilast) once daily in the morning Day 15 and thereafter.

EMBODIMENTS

1. An oral dosage form comprising:
   a. a core tablet comprising
      (i) a drug layer comprising apremilast and hypromellose acetate succinate (HPMCAS) in an amorphous solid dispersion; and
      (ii) a swellable layer comprising one or more swellable polymers; and
   b. a coating layer disposed on the core tablet,
wherein the oral dosage form surface comprises at least one drug release orifice.
2. The oral dosage form of embodiment 1, wherein the apremilast is present in an amount of 6-15 wt % of the core tablet.
3. The oral dosage form of embodiment 1 or 2, wherein the solid dispersion is spray-dried.
4. The oral dosage form of any one of embodiments 1-3, wherein the HPMCAS is present in an amount of 6-15 wt % of the core tablet.
5. The oral dosage form of any one of embodiments 1-4, wherein apremilast and HPMCAS are present in a weight ratio of 45:55 to 55:45 in the core tablet.
6. The oral dosage form of embodiment 5, wherein apremilast and HPMCAS are present in a weight ratio of 48:52 to 52:48.
7. The oral dosage form of embodiment 5, wherein apremilast and HPMCAS are present in a weight ratio of 50:50.
8. The oral dosage form of any one of embodiments 1-7, wherein the drug layer further comprises one or more of a water soluble polymer, a diluent, an osmotic agent, and a lubricant.
9. The oral dosage form of embodiment 8, wherein the water soluble polymer is present in an amount of 30-55 wt % of the core tablet.
10. The oral dosage form of embodiment 8 or 9, wherein the water soluble polymer comprises polyethylene oxide.
11. The oral dosage form of embodiment 10, wherein the polyethylene oxide has an average molecular weight of 200,000-600,000 Da.
12. The oral dosage form of embodiment 11, wherein the drug layer comprises polyethylene oxide having an average molecular weight of 200,000 Da.
13. The oral dosage form of embodiment 11, wherein the drug layer comprises polyethylene oxide having an average molecular weight of 300,000 Da.
14. The oral dosage form of embodiment 11, wherein the drug layer comprises polyethylene oxide having an average molecular weight of 600,000 Da.
15. The oral dosage form of any one of embodiments 8-14, wherein the water soluble polymer and apremilast are present in a weight ratio of 2 to 6:1, in the drug layer.
16. The oral dosage form of any one of embodiments 8-15, wherein the diluent comprises mannitol.
17. The oral dosage form of any one of embodiments 8-16, wherein the diluent is present in an amount of 2-7 wt % of the core tablet.
18. The oral dosage form of any one of embodiments 8-17, wherein the drug layer comprises intragranular diluent and extragranular diluent.
19. The oral dosage form of any one of embodiment 8-18, wherein the osmotic agent is present in the drug layer in an amount of 3-8 wt % of the core tablet.
20. The oral dosage form of any one of embodiments 8-19, wherein the osmotic agent in the drug layer comprises sodium chloride.
21. The oral dosage form of any one of embodiments 8-20, wherein the lubricant comprises magnesium stearate.
22. The oral dosage form of any one of embodiments 8-21, wherein the lubricant of the drug layer is present in an amount of 0.05-0.5 wt % of the core tablet.
23. The oral dosage form of any one of embodiments 1-22, wherein the drug layer further comprises extragranular glidant, extragranular lubricant, or both.
24. The oral dosage form of embodiment 23, wherein the extragranular glidant comprises silicon dioxide.
25. The oral dosage form of embodiment 23 or 24, wherein the extragranular lubricant comprises magnesium stearate.
26. The oral dosage form of any one of embodiments 1-25, wherein the drug layer and swellable layer are present in a weight ratio of 2:1 in the core tablet.
27. The oral dosage form of any one embodiments 1-26, wherein the swellable polymer comprises polyethylene oxide.
28. The oral dosage form of embodiment 27, wherein the polyethylene oxide has an average molecular weight of 5,000,000 Da.
29. The oral dosage form of any one of embodiments 1-28, wherein the swellable layer further comprises one or more of an osmotic agent, a diluent, a lubricant, and a colorant.
30. The oral dosage form of embodiment 29, wherein the osmotic agent of the swellable layer comprises sodium chloride.
31. The oral dosage form of embodiment 29 or 30, wherein the osmotic agent in the swellable layer is present in an amount of 2.5-3.5 wt % of the core tablet.
32. The oral dosage form of any one of embodiments 29-31, wherein the diluent of the swellable layer comprises microcrystalline cellulose.
33. The oral dosage form of any one of embodiments 29-32, wherein the diluent in the swellable layer is present in an amount of 7-10 wt % of the core tablet.
34. The oral dosage form of any one of embodiments 29-33, wherein the lubricant of the swellable layer comprises magnesium stearate.

35. The oral dosage form of any one of embodiments 29-34, where the lubricant of the swellable layer is present in an amount of 0.05-0.5 wt % of the core tablet.
36. The oral dosage form of any one of embodiments 29-35, wherein the colorant comprises iron oxide red.
37. The oral dosage form of any one of embodiments 29-36, where the colorant is present in an amount of 0.05-0.5 wt % of the core tablet.
38. The oral dosage form of any one of embodiments 1-37, wherein the coating comprises cellulose acetate and polyethylene glycol.
39. The oral dosage form of embodiment 38, wherein the cellulose acetate and polyethylene glycol are present in a weight ratio 3.5 to 4.5:1 in the coating.
40. The oral dosage form of any one of embodiments 1-39, wherein the coating comprises 6.5-8.5 wt % of the total weight of the oral dosage form.
41. The oral dosage form of embodiment 40, wherein the coating comprises 7.5 wt % of the total weight of the oral dosage form.
42. The oral dosage form of any one of embodiments 141, further comprising a sub-coat layer between the core tablet and the coating layer.
43. The oral dosage form of embodiment 42, wherein the sub-coat layer comprises hydroxypropyl methylcellulose.
44. The oral dosage form of embodiment 42 or 43, wherein the sub-coat layer is present in an amount of 2-4 wt % of the oral dosage form.
45. The oral dosage form of embodiment 44, wherein the sub-coat layer is present in an amount of 2.3 wt % of the oral dosage form.
46. The oral dosage form of embodiment 44, wherein the sub-coat layer is present in an amount of 3.4 wt % of the oral dosage form.
47. The oral dosage form of any one of embodiments 1-46, wherein the drug layer comprises an intragranular portion and an extragranular portion.
48. The oral dosage form of embodiment 47, wherein the extragranular portion comprises a lubricant and a glidant.
49. The oral dosage form of embodiment 48, wherein the extragranular portion further comprises a diluent.
50. The oral dosage form of embodiment 49, wherein the lubricant comprises magnesium stearate, the glidant comprises silicon dioxide, and the diluent comprises mannitol.
51. The oral dosage form of any one of embodiments 47-50, wherein the intragranular portion comprises apremilast, HPMCAS, polyethylene oxide, and mannitol, and an intragranular lubricant.
52. The oral dosage form of embodiment 51, wherein the intragranular lubricant comprises magnesium stearate.
53. The oral dosage form of any one of embodiments 49-52, wherein the mannitol is present in both the intragranular portion and the extragranular portion.
54. The oral dosage form of embodiment 53, comprising 55-57% of the total mannitol present is in the intragranular portion and 43-45% of the total mannitol present is in the extragranular portion.
55. The oral dose form of any one of embodiments 47-54, wherein the swellable layer further comprises a lubricant.
56. The oral dosage form of embodiment 55, wherein the lubricant of the swellable layer comprises magnesium stearate.
57. The oral dosage form of any one of embodiments 47-56, wherein the drug layer intragranular portion comprises sodium chloride.
58. The oral dosage form of any one of embodiments 47-57, further comprising a color coat layer in an amount of 3-5 wt % of the oral dosage form.
59. The oral dosage form of embodiment 58, wherein the color coat layer is present in an amount of 3.4 wt % of the oral dosage form.
60. An oral dosage form comprising:
    a. a core tablet comprising
        (i) a drug layer comprising 8-11 wt % apremilast based upon total core tablet weight, 8-11 wt % hypromellose acetate succinate (HPMCAS) based upon total core tablet weight, 2-7 wt % mannitol based upon total core tablet weight, 40-45 wt % polyethylene oxide with molecular weight of 200,000 Da based upon total core tablet weight, 0.1-0.5 wt % magnesium stearate based upon total core tablet weight, and 0.1-0.5 wt % colloidal silicon dioxide based upon total core tablet weight, wherein the apremilast and HPMCAS are in a solid dispersion;
        (ii) a swellable layer comprising 18-25 wt % polyethylene oxide with molecular weight of 5,000,000 Da based upon total core tablet weight, 7-10 wt % microcrystalline cellulose based upon total core tablet weight, 1.5-3.5 wt. % sodium chloride based upon total core tablet weight, 0.01-0.2 wt % iron oxide based upon total core tablet weight, and 0.05-0.3 wt % magnesium stearate based upon total core tablet weight; and
    b. a coating layer disposed on the core tablet and comprising cellulose acetate and polyethylene glycol; wherein the oral dosage form surface comprises at least one drug release orifice.
61. The oral dosage form of embodiment 60 comprising:
    a. a core tablet comprising
        (i) a drug layer comprising 75 mg apremilast, 75 mg hypromellose acetate succinate (HPMCAS), 22.1 mg mannitol, 314.8 mg polyethylene oxide with molecular weight of 200,000 Da, 2.4 mg magnesium stearate, and 2.5 mg colloidal silicon dioxide, wherein the apremilast and HPMCAS are in a solid dispersion;
        (ii) a swellable layer comprising 159.6 mg polyethylene oxide with molecular weight of 5,000,000 Da, 63.4 mg microcrystalline cellulose, 21.1 mg sodium chloride, 0.5 mg iron oxide, and 1.2 mg magnesium stearate; and
    b. a coating layer disposed on the core tablet and comprising cellulose acetate and polyethylene glycol; wherein the oral dosage form surface comprises at least one drug release orifice.
62. The oral dosage form of embodiment 60 comprising:
    a. a core tablet comprising
        (i) a drug layer comprising 55 mg apremilast, 55 mg hypromellose acetate succinate (HPMCAS), 16.2 mg mannitol, 230.9 mg polyethylene oxide with molecular weight of 200,000 Da, 1.7 mg magnesium stearate, and 1.8 mg colloidal silicon dioxide, wherein the apremilast and HPMCAS are in a solid dispersion;
        (ii) a swellable layer comprising 117 mg polyethylene oxide with molecular weight of 5,000,000 Da, 46.5 mg microcrystalline cellulose, 15.5 mg sodium chloride, 0.4 mg iron oxide, and 0.9 mg magnesium stearate; and b. a coating layer disposed on the core tablet and comprising cellulose acetate and polyethylene glycol; wherein the oral dosage form surface comprises at least one drug release orifice.

63. The oral dosage form of embodiment 60 comprising:
   a. a core tablet comprising
      (i) a drug layer comprising 27.5 mg apremilast, 27.5 mg hypromellose acetate succinate (HPMCAS), 8.1 mg mannitol, 115.6 mg polyethylene oxide with molecular weight of 200,000 Da, 1.0 mg magnesium stearate, and 0.9 mg colloidal silicon dioxide, wherein the apremilast and HPMCAS are in a solid dispersion;
      (ii) a swellable layer comprising 58.6 mg polyethylene oxide with molecular weight of 5,000,000 Da, 23.3 mg microcrystalline cellulose, 7.8 mg sodium chloride, 0.2 mg iron oxide, and 0.5 mg magnesium stearate; and
   b. a coating layer disposed on the core tablet and comprising cellulose acetate and polyethylene glycol; wherein the oral dosage form surface comprises at least one drug release orifice.

64. An oral dosage form comprising:
   a. a core tablet comprising
      (i) a drug layer comprising 9-15 wt. % apremilast based upon total core tablet weight, 10-15 wt % hypromellose acetate succinate (HPMCAS) based upon total core tablet weight, 0-27 wt % mannitol based upon total core tablet weight, 30-40 wt % polyethylene oxide with molecular weight of 200,000 to 300,000 Da or a mixture thereof based upon total core tablet weight, 2-8 wt % sodium chloride based upon total core tablet weight, 0.1-0.5 wt % magnesium stearate based upon total core tablet weight, and 0.1-0.5 wt % colloidal silicon dioxide based upon total core tablet weight, wherein the apremilast and HPMCAS are in a solid dispersion;
      (ii) a swellable layer comprising 15-25 wt % polyethylene oxide with molecular weight of 5,000,000 Da based upon total core tablet weight, 5-10.0 wt % microcrystalline cellulose based upon total core tablet weight, 2-4 wt % sodium chloride based upon total core tablet weight, 0.01-0.1 wt % iron oxide based upon total core tablet weight, and 0.05-0.3 wt % magnesium stearate based upon total core tablet weight; and
   b. a coating layer disposed on the core tablet and comprising cellulose acetate and polyethylene glycol; wherein the oral dosage form surface comprises at least one drug release orifice.

65. The oral dosage form of embodiment 64 comprising:
   a. a core tablet comprising
      (i) a drug layer comprising 100 mg apremilast, 100 mg hypromellose acetate succinate (HPMCAS), 301.4 mg polyethylene oxide with molecular weight of 200,000 to 300,000 Da or a mixture thereof, 26.7 mg sodium chloride, 2.6 mg magnesium stearate, and 2.7 mg colloidal silicon dioxide, wherein the apremilast and HPMCAS are in a solid dispersion;
      (ii) a swellable layer comprising 173.1 mg polyethylene oxide with molecular weight of 5,000,000 Da, 68.8 mg microcrystalline cellulose, 22.9 mg sodium chloride, 0.5 mg iron oxide, and 1.3 mg magnesium stearate; and
   b. a coating layer disposed on the core tablet and comprising cellulose acetate and polyethylene glycol; wherein the oral dosage form surface comprises at least one drug release orifice.

66. The oral dosage form of embodiment 64 comprising:
   a. a core tablet comprising
      (i) a drug layer comprising 100 mg apremilast, 100 mg hypromellose acetate succinate (HPMCAS), 274.6 mg polyethylene oxide with molecular weight of 300,000 Da, 53.3 sodium chloride, 2.6 mg magnesium stearate, and 2.7 mg colloidal silicon dioxide, wherein the apremilast and HPMCAS are in a solid dispersion;
      (ii) a swellable layer comprising 173.1 mg polyethylene oxide with molecular weight of 5,000,000 Da, 68.8 mg microcrystalline cellulose, 22.9 mg sodium chloride, 0.5 mg iron oxide, and 1.3 mg magnesium stearate; and
   b. a coating layer disposed on the core tablet and comprising cellulose acetate and polyethylene glycol; wherein the oral dosage form surface comprises at least one drug release orifice.

67. The oral dosage form of embodiment 64 comprising:
   a. a core tablet comprising
      (i) a drug layer comprising 75 mg apremilast, 75 mg hypromellose acetate succinate (HPMCAS), 226.0 mg polyethylene oxide with molecular weight of 200,000 to 300,000 Da or a mixture thereof, 20.0 mg sodium chloride, 2.0 mg magnesium stearate, and 2.0 mg colloidal silicon dioxide, wherein the apremilast and HPMCAS are in a solid dispersion;
      (ii) a swellable layer comprising 129.8 mg polyethylene oxide with molecular weight of 5,000,000 Da, 51.6 mg microcrystalline cellulose, 17.2 mg sodium chloride, 0.4 mg iron oxide, and 1.0 mg magnesium stearate; and
   b. a coating layer disposed on the core tablet and comprising cellulose acetate and polyethylene glycol; wherein the oral dosage form surface comprises at least one drug release orifice.

68. The oral dosage form of embodiment 64 comprising:
   a. a core tablet comprising
      (i) a drug layer comprising 75 mg apremilast, 75 mg hypromellose acetate succinate (HPMCAS), 206.0 mg polyethylene oxide with molecular weight of 300,000 Da, 40.0 mg sodium chloride, 2.0 mg magnesium stearate, and 2.0 mg colloidal silicon dioxide, wherein the apremilast and HPMCAS are in a solid dispersion;
      (ii) a swellable layer comprising 129.8 mg polyethylene oxide with molecular weight of 5,000,000 Da, 51.6 mg microcrystalline cellulose, 17.2 mg sodium chloride, 0.4 mg iron oxide, and 1.0 mg magnesium stearate; and
   b. a coating layer disposed on the core tablet and comprising cellulose acetate and polyethylene glycol; wherein the oral dosage form surface comprises at least one drug release orifice.

69. The oral dosage form of embodiment 64 comprising:
   a. a core tablet comprising
      (i) a drug layer comprising 55 mg apremilast, 55 mg hypromellose acetate succinate (HPMCAS), 165.7 mg polyethylene oxide with molecular weight of 200,000 to 300,000 Da or a mixture thereof, 14.7 mg sodium chloride, 1.4 mg magnesium stearate, and 1.5 mg colloidal silicon dioxide, wherein the apremilast and HPMCAS are in a solid dispersion;
(ii) a swellable layer comprising 95.2 mg polyethylene oxide with molecular weight of 5,000,000 Da, 37.8 mg microcrystalline cellulose, 12.6 mg sodium chloride, 0.3 mg iron oxide, and 0.7 mg magnesium stearate; and
b. a coating layer disposed on the core tablet and comprising cellulose acetate and polyethylene glycol; wherein the oral dosage form surface comprises at least one drug release orifice.

70. The oral dosage form of embodiment 64 comprising:
a. a core tablet comprising
(i) a drug layer comprising 55 mg apremilast, 55 mg hypromellose acetate succinate (HPMCAS), 151.1 mg polyethylene oxide with molecular weight of 300,000 Da, 29.3 mg sodium chloride, 1.4 mg magnesium stearate, and 1.5 mg colloidal silicon dioxide, wherein the apremilast and HPMCAS are in a solid dispersion;
(ii) a swellable layer comprising 95.2 mg polyethylene oxide with molecular weight of 5,000,000 Da, 37.8 mg microcrystalline cellulose, 12.6 mg sodium chloride, 0.3 mg iron oxide, and 0.7 mg magnesium stearate; and
b. a coating layer disposed on the core tablet and comprising cellulose acetate and polyethylene glycol; wherein the oral dosage form surface comprises at least one drug release orifice.

71. The oral dosage form of embodiment 64 comprising:
a. a core tablet comprising
(i) a drug layer comprising 27.5 mg apremilast, 27.5 mg hypromellose acetate succinate (HPMCAS), 82.9 mg polyethylene oxide with molecular weight of 200,000 to 300,000 Da or a mixture thereof, 7.3 mg sodium chloride, 0.8 mg magnesium stearate, and 0.7 mg colloidal silicon dioxide, wherein the apremilast and HPMCAS are in a solid dispersion;
(ii) a swellable layer comprising 47.6 mg polyethylene oxide with molecular weight of 5,000,000 Da, 18.9 mg microcrystalline cellulose, 6.3 mg sodium chloride, 0.1 mg iron oxide, and 0.4 mg magnesium stearate; and
b. a coating layer disposed on the core tablet and comprising cellulose acetate and polyethylene glycol; wherein the oral dosage form surface comprises at least one drug release orifice.

72. The oral dosage form of embodiment 64 comprising:
a. a core tablet comprising
(i) a drug layer comprising 27.5 mg apremilast, 27.5 mg hypromellose acetate succinate (HPMCAS), 75.5 mg polyethylene oxide with molecular weight of 300,000 Da, 14.7 mg sodium chloride, 0.4 mg magnesium stearate, and 0.7 mg colloidal silicon dioxide, wherein the apremilast and HPMCAS are in a solid dispersion;
(ii) a swellable layer comprising 47.6 mg polyethylene oxide with molecular weight of 5,000,000 Da, 18.9 mg microcrystalline cellulose, 6.3 mg sodium chloride, 0.1 mg iron oxide, and 0.4 mg magnesium stearate; and
b. a coating layer disposed on the core tablet and comprising cellulose acetate and polyethylene glycol; wherein the oral dosage form surface comprises at least one drug release orifice.

73. A method of treating a patient suffering from a disease or disorder ameliorated by inhibiting PDE4 comprising administering to the patient the oral dosage form of any one of embodiments 1-72 once daily under fed conditions.

74. The method of embodiment 73, wherein the disease or disorder is psoriasis, psoriatic arthritis, or Behcet's disease.

75. The method of embodiment 73, wherein the disease or disorder is colitis, inflammatory bowel disease, or hidradenitis suppurativa.

76. The method of embodiment 75, wherein the disease or disorder is colitis.

77. The method of embodiment 76, wherein the colitis is ulcerative colitis.

78. The method of embodiment 75, wherein the disease or disorder is inflammatory bowel disease.

79. The method of embodiment 75, wherein the disease or disorder is hidradenitis suppurativa.

EXAMPLES

The following examples further illustrate the disclosed methods of treatment, but of course, should not be construed as in anyway limiting its scope.

The following abbreviations are used in the Examples: SCT refers to swellable core technology; TAB refers to tablet; SDD refers to amorphous spray-dried dispersion; APR refers to amorphous apremilast; HPMCAS refers to hypromellose acetate succinate; HPMC refers to hydroxypropyl methylcellulose; DL refers to drug layer; SL refers to swellable layer; CL refers to coating layer; PEO refers to polyethylene oxide; PEG refers to polyethylene glycol; Mg refers to magnesium; IG refers to intragranular; EG refers to extragranular; MCC refers to microcrystalline cellulose; NaCl refers to sodium chloride; MW refers to molecular weight; $cSiO_2$ refers to colloidal silicon dioxide; CA refers to cellulose acetate; RR refers to release rate; SRC refers to standard round concave; SEM refers to scanning electron microscopy, inWC refers to inches of water column; $AUC_{0-\infty}$ refers to area under the plasma concentration-time curve calculated from time zero to infinity; $AUC_{0-t}$ refers to area under the concentration-time curve calculated from time zero to the last measured time point; CL/F refers to apparent clearance of drug from plasma after extravascular administration; $C_{max}$ refers to observed maximum concentration; $C_{trough}$ refers to observed plasma concentration at the end of the dosing interval; CI refers to confidence interval; CV % refers to coefficient of variation; $t_{1/2}$ refers to terminal elimination half-life; $t_{lag}$ refers to delay between time of administration and start of absorption lag time; $T_{max}$ refers to time to $C_{max}$; Vz/F refers to apparent volume of distribution during the terminal phase; $F_{rel1}$ refers to relative bioavailability of each test formulation compared to the reference formulation; $F_{rel2}$ refers to relative bioavailability of each dose-normalized test formulation compared to the dose-normalized reference formulation IR tablet; and RA refers to ratio of accumulation based on Day 1 and Day 5 area under the plasma concentration-time curve during a 24-hour period.

Example 1

This example demonstrates the preparation of amorphous spray-dried solid dispersions comprising 48 wt % and 52 wt % apremilast loading were manufactured using a PSD-1 scale spray dryer at a batch size of 2 kg for each loading.

Solutions were prepared at 48:52 APR:HPMCAS-LG and 52:48 APR:HPMCAS-LG at 12% total solids in acetone (Tables 1 and 2). The solutions were sprayed in order of increasing drug loading, with a minor clean performed between the two sprays (e.g., rinsing out the chamber and duct work with water and detergent (e.g., alkaline detergent; CIP-100), and flushing with acetone through the feed pump). Drying kinetics and thermodynamics were kept consistent with historical 50% apremilast SDD runs. The 48% drug loading in SDD had a wet yield of 82%, followed by a 67% wet yield for the 52% drug loading SDD. Wet yields were calculated from total net weight collected from the spray dryer, not-including startup/shut down quantities and pre wet SDD sampling, and based on the ingoing 2 kg of solids. The averaged run conditions and wet yields for both SDD batches are listed in Table 3.

TABLE 1

48:52 APR:HPMCAS-LG SDD
48:52 APR:HPMCAS-LG at 12 wt % Solids in Acetone

| Ingredient | % of Blend | mg/g in SDD |
| --- | --- | --- |
| apremilast | 5.76 | 480.0 |
| HPMCAS-LG | 6.24 | 520.0 |
| Acetone | 88.00 | 0.0 |

TABLE 2

52:48 APR:HPMCAS-LG SDD
52:48 APR:HPMCAS-LG at 12 wt % Solids in Acetone

| Ingredient | % of Blend | mg/g SDD |
| --- | --- | --- |
| apremilast | 6.24 | 520.0 |
| HPMCAS-LG | 5.76 | 480.0 |
| Acetone | 88.00 | 0.0 |

TABLE 3

Run Condition Averages and Wet Yield for 48% And 52% APR SDD

| SDD Composition | 48:52 APR: HPMCAS-LG | 48:52 APR: HPMCAS-LG |
| --- | --- | --- |
| N$_2$ Flow Rate (g/min) | 1850 | 1854 |
| Solution Flow Rate (g/min) | 201 | 200 |
| Atomization Pressure (psi) | 496 | 517 |
| Inlet Temp (° C.) | 106 | 106 |
| Outlet Temp (° C.) | 41 | 41 |
| Cyclone Pressure Differential (inWC) | 11 | 11 |
| Filter DP (inWC) | 5 | 5 |
| Wet Yield | 82% | 67% |

Once all wet SDD samples were collected, bulk SDD from both drug loadings were secondary dried using a convection tray dryer at 40° C. and 15% relative humidity (RH). The 48% APR SDD was dried for 1100 minutes and the 52% APR SDD was dried for 505 minutes. The dry yield for the 48% and 52% drug loading SDDs were 78% and 64%, respectively, as calculated from total net weight collected from the tray dryer, including dry SDD samples as well as wet SDD samples assuming a 5% solvent loss, and based on the 2 kg of ingoing solids.

Dry SDD from each drug loading was then characterized for particle size distribution using laser diffraction with a Malvern Mastersizer 2000 (Malvern Panalytical; Malvern, United Kingdom). The average particle size data are shown in Table 4. Both drug loadings had the same particle size of 33 μm (D[4,3]), indicating that the slight difference in composition does not impact particle size.

TABLE 4

Particle Size Data for 48% and 52% Apremilast SDD.

| | Averages | | | | | |
| --- | --- | --- | --- | --- | --- | --- |
| Sample | D(v 0.1) μm | D(v 0.5) μm | D(v 0.9) μm | D[3, 2] μm | D[4, 3] μm | Span |
| 48:52 APR:HPMCAS-LG Dry SDD | 8 | 30 | 63 | 13 | 33 | 1.9 |
| 52:48 APR:HPMCAS-LG Dry SDD | 7 | 29 | 64 | 13 | 33 | 2.0 |

*values Obtained Using a Dispersive Air Pressure of 1 Bar and a Vibration Feed Rate of 65%

Characterization of the SDDs is summarized in Table 5 and includes residual acetone by gas chromatography (GC), crystallinity by powder X-ray diffraction (PXRD), thermal properties by modulated differential scanning calorimetry (mDSC), assay and related substances by high performance liquid chromatography (HPLC), performance by microcentrifuge dissolution and morphology by scanning electron microscopy (SEM).

TABLE 5

Physical Characterization for 48% and 52% Apremilast SDD

| SDD Composition | 48:52 APR: HPMCAS-LG | 52:48 APR: HPMCAS-LG |
| --- | --- | --- |
| Residual Acetone Before Secondary Drying | 3.7 wt % | 3.8 wt % |
| Residual Acetone After Secondary Drying | 0.07 wt % | 0.17 wt % |
| Residual Water After Secondary Drying (KF) | 0.81 wt %, 6.0% RSD | 0.72 wt %, 4.7% RSD |
| Appearance by SEM | Smooth collapsed and uncollapsed spheres, no evidence of crystals | Smooth collapsed and uncollapsed spheres, no evidence of crystals |
| Crystallinity by PXRD | None Detected | None Detected |
| Glass Transition Temperature by mDSC | 79.7° C. | 80.5° C. |
| Assay by HPLC (wt % APR) | 47.1 wt % | 50.8 wt % |
| Related Substances | None Detected | None Detected |
| Microcentrifuge Dissolution | $C_{maxSIF1200}$ = 504 μg/mL, $AUC_{SIF}$ = 43,180 min*μg/mL | $C_{maxSIF1200}$ = 479 μg/mL, $AUC_{SIF}$ = 40,780 min* μg/mL |

As shown in Table 5, there was no significant difference in residual acetone content of the 48% and 52% APR SDDs after spray drying and before secondary drying. The 52% APR SDD had slightly higher residual acetone after secondary drying due to a shorter drying time, but both batches were below the ICH limit of 5000 ppm. The 48% APR SDD was dried for 1100 minutes and the 52% APR SDD was dried for 505 minutes. Similarly, there was no measurable difference in the glass transition temperatures.

SEM analysis showed both the 48% and 52% APR SDD consisting of smooth collapsed and uncollapsed spheres, with no evidence of crystallinity. The 52% APR SDD appeared to have a greater number of uncollapsed spheres compared to the 48% APR SDD, as well as a greater number of broken particles.

SDD Stability Studies—Wet SDD Hold Time Study

A 48% and a 52% drug loading (by weight) SDD were manufactured using a PSD-1 scale spray dryer as described herein. Wet SDD from each batch was stored in LDPE bags inside air-tight stainless steel containers and held at 27° C. for up to 30 days. At 10, 20 and 30 days, samples were removed from each batch for characterization by SEM, mDSC, PXRD, assay and related substances by HPLC, residual solvent and non-sink dissolution (Microcentrifuge Dissolution Test).

SEM analysis showed both the 48% and 52% APR SDDs contain smooth collapsed and un-collapsed spheres, with no evidence of fusing or crystallinity. No changes in morphology or physical state were observed after 30 days storage before secondary drying. PXRD analysis showed that no crystallization occurred throughout the 30 day stability study for both the 48% and 52% APR SDDs. Moreover, no morphological changes indicating crystallization were observed within the capability of the method of SEM analysis. The DSC thermograms indicated no measurable difference in the Tg of the stability samples compared to the dry SDD. Assay and related substances showed no increase in impurities over the 30 day stability hold. Similarly, the microcentrifuge dissolution results showed no differences in performance over the 30 days Example 2

This example demonstrates tablet dosage forms in accordance with embodiments of the disclosure.

Fourteen apremilast SCT dosage formulations were prepared using the 8 drug layers (DL) and 6 swellable layers (SL) shown in Tables 6 and 7. The tablet cores were coated with a coating layer comprising CA and PEG as indicated in Table 8. The drug layer compositions and swellable layer compositions are shown in Tables 9 and 10.

TABLE 6

Drug Layers (DL) 1-8

| DL | APR: HPMCAS | PEO 200 kDa | Mg Stearate (IG) | Mg Stearate (EG) |
|---|---|---|---|---|
| DL-1 | 50:50 | − | − | + |
| DL-2 | 50:50 | + | − | − |
| DL-3 | 50:50 | − | + | − |
| DL-4 | 50:50 | + | + | + |
| DL-5 | 50:50 | 0 | 0 | 0 |
| DL-6 | 50:50 | 0 | 0 | 0 |
| DL-7 | 48:52 | 0 | 0 | 0 |

TABLE 6-continued

Drug Layers (DL) 1-8

| DL | APR: HPMCAS | PEO 200 kDa | Mg Stearate (IG) | Mg Stearate (EG) |
|---|---|---|---|---|
| DL-8 | 52:48 | 0 | 0 | 0 |
| + | | 105.0% | 105.0% | 105.0% |
| − | | 95.0% | 95.0% | 95.0% |
| 0 | | 100.0% | 100.0% | 100.0% |

TABLE 7

Swellable Layers (SL) 1-6

| SL | PEO 5000 kDa | NaCl | Mg Stearate |
|---|---|---|---|
| SL-1 | − | − | + |
| SL-2 | + | − | − |
| SL-3 | − | + | − |
| SL-4 | + | + | + |
| SL-5 | 0 | 0 | 0 |
| SL-6 | 0 | 0 | 0 |
| + | 105.0% | 105.0% | 105.0% |
| − | 95.0% | 95.0% | 95.0% |
| 0 | 100.0% | 100.0% | 100.0% |

Percent changes of excipient addition based on standard formulation, 75 mg Tablets containing DL5-8 and SL5-6

TABLE 8

Tablets 1-14

| Tablet | DL ID | SL ID | CA:PEG Coating Ratio |
|---|---|---|---|
| 1 | DL-6 | SL-1 | 80/20 |
| 2 | DL-6 | SL-2 | 80/20 |
| 3 | DL-6 | SL-3 | 80/20 |
| 4 | DL-6 | SL-4 | 80/20 |
| 5 | DL-6 | SL-5 | 80/20 |
| 6 | DL-1 | SL-6 | 80/20 |
| 7 | DL-2 | SL-6 | 80/20 |
| 8 | DL-3 | SL-6 | 80/20 |
| 9 | DL-4 | SL-6 | 80/20 |
| 10 | DL-5 | SL-6 | 80/20 |
| 11 | DL-7 | SL-6 | 80/20 |
| 12 | DL-8 | SL-6 | 80/20 |
| 13 | DL-6 | SL-6 | 81/19 |
| 14 | DL-6 | SL-6 | 79/21 |

*For all tablet cores: DL is 491.8 mg; SL is 245.9 mg; and tablet core weight is 737.7 mg

TABLE 9

Drug layer compositions

| | Composition | | | | | | | | | |
|---|---|---|---|---|---|---|---|---|---|---|
| | DL5-8 | | DL1 | | DL2 | | DL3 | | DL4 | |
| Ingredient | % of blend | mg/tab | % of blend | mg/tab | % of blend | mg/tab | % of blend | mg/tab | % of blend | mg/tab |
| Intragranular | | | | | | | | | | |
| APR:HPMCAS | 30.50 | 150.0 | 30.50 | 150.0 | 30.50 | 150.0 | 30.50 | 150.0 | 30.50 | 150.0 |
| PEO 200 kDa | 64.0 | 314.75 | 60.80 | 299.01 | 67.20 | 330.49 | 60.80 | 299.01 | 67.20 | 330.49 |
| Mannitol (spray-dried) | 2.50 | 12.3 | 4.28 | 21.04 | 0.74 | 3.62 | 4.28 | 21.04 | 0.71 | 3.48 |
| Mg stearate | 0.25 | 1.23 | 0.24 | 1.17 | 0.24 | 1.17 | 0.26 | 1.29 | 0.26 | 1.29 |

TABLE 9-continued

Drug layer compositions

| | Composition | | | | | | | | | |
|---|---|---|---|---|---|---|---|---|---|---|
| | DL5-8 | | DL1 | | DL2 | | DL3 | | DL4 | |
| Ingredient | % of blend | mg/tab | % of blend | mg/tab | % of blend | mg/tab | % of blend | mg/tab | % of blend | mg/tab |
| Extragranular | | | | | | | | | | |
| cSiO$_2$ (fumed) | 0.50 | 2.46 | 0.50 | 2.46 | 0.50 | 2.46 | 0.50 | 2.46 | 0.50 | 2.46 |
| Mannitol (spray-dried) | 2.0 | 9.84 | 3.42 | 16.83 | 0.59 | 2.90 | 3.42 | 16.83 | 0.57 | 2.79 |
| Mg stearate | 0.25 | 1.23 | 0.26 | 1.29 | 0.24 | 1.17 | 0.24 | 1.17 | 0.26 | 1.29 |
| Total | 100.0 | 491.8 | 100.0 | 491.8 | 100.0 | 491.8 | 100.0 | 491.8 | 100.0 | 491.8 |

TABLE 10

Swellable layer compositions

| | Composition | | | | | | | | | |
|---|---|---|---|---|---|---|---|---|---|---|
| | SL5-6 | | SL1 | | SL2 | | SL3 | | SL4 | |
| Ingredient | % of blend | mg/tab | % of blend | mg/tab | % of blend | mg/tab | % of blend | mg/tab | % of blend | mg/tab |
| PEO 5000 kDa | 64.90 | 159.59 | 61.66 | 151.61 | 68.15 | 167.57 | 61.66 | 151.61 | 68.15 | 167.57 |
| MCC | 25.80 | 63.44 | 29.45 | 72.42 | 23.01 | 56.58 | 28.64 | 70.43 | 22.10 | 54.34 |
| NaCl | 8.60 | 21.15 | 8.17 | 20.09 | 8.17 | 20.09 | 9.03 | 22.21 | 9.03 | 22.21 |
| Iron oxide Red | 0.20 | 0.49 | 0.20 | 0.49 | 0.20 | 0.49 | 0.20 | 0.49 | 0.20 | 0.49 |
| Mg stearate | 0.50 | 1.23 | 0.53 | 1.29 | 0.48 | 1.17 | 0.48 | 1.17 | 0.53 | 1.29 |
| Total | 100.0 | 245.9 | 100.0 | 245.9 | 100.0 | 245.9 | 100.0 | 245.9 | 100.0 | 245.9 |

Process

Drug layer blends were prepared using the procedure described herein, including blending, milling, and dry granulation using roller compaction. A pre-granulated blend density of 0.48 g/mL was assumed to calculate fill volumes. Blender speeds were determined by keeping the Froude number constant at approximately 0.05 across all scales.

For the drug layer pre blend, the following components were added to the blender: polyethylene oxide (e.g., PolyOx WSR-N80, MW of 200 kDa), SDD, and mannitol and blended. The pre-blend was then passed through the conical mill at slow speed, followed by blending. The lubricant (e.g., magnesium stearate) was screened (20-mesh), added to the blender, and blended. This blended mixture was then granulated using a roller compactor (see Table 11 for parameters). The resulting granulation was discharged into a container. Extragranular excipients (e.g., colloidal silicon dioxide and mannitol) were added to the blender and mixed. The extragranular excipient blend was then passed through the conical mill at a slow speed. The granulation and this screened extragranular blend were then combined in the blender and mixed. Lubricant (e.g., magnesium stearate was screened (20-mesh) and added to the blender with mixing. The drug layer was discharged after blending.

The swellable layer was prepared using a similar procedure assuming a bulk density of 0.41 g/mL to calculate fill volumes. The osmotic agent (e.g., sodium chloride) and colorant (e.g., iron oxide) were combined, blended using a low speed. The sodium chloride and iron oxide mixture was then passed through a conical mill at a slow speed. The swellable polymer (e.g., polyethylene oxide) and diluent (e.g., microcrystalline cellulose) were added to the screened mixture and blended. The combined, blended mixture is milled and blended again. Lubricant (e.g., magnesium stearate) is screened (20-mesh), added to the blender, and blended. The blended swellable layer mixture is discharged.

Roller compaction was conducted using the process parameters outlined in Table 11 with a target solid fraction of 0.65 in the range of 0.60-0.70.

TABLE 11

Roller compaction parameters

| Parameters | Settings |
|---|---|
| Roll Settings | |
| Master roll (lower, left position) | Knurled |
| Second roll (upper, right position) | Knurled |
| Compression force | 2.0 kN/cm |
| Press roller start speed | 0.5 rpm |
| Press roller speed | 4 (±1) rpm |
| Gap width | 2 (±0.5) mm |
| PID | 3:8000:0 (unitless:msec:msec) |
| Feed Factor | 0.7 |
| Density Ratio | 0.7 |
| Feed Settings | |
| Agitator Speed (rpm) | 5 |
| Tamp/feed ratio | 300% |
| Gap-control activated (on/off) | On |
| Torque control (on/off) | Off |

TABLE 11-continued

Roller compaction parameters

| Parameters | Settings |
|---|---|
| Granulator Settings | |
| Granulator type | Star rotor |
| Granulator screen type | Square wire mesh |
| Granulator screen size | 1.0 mm |
| Granulator rotor gap | 1.0 mm (0.7-1.1 mm) |
| Granulator speed | 60 rpm |
| Granulator CW/CCW degrees | 360/400 |

Ribbon solid fractions for each drug layer blend were within the range of 0.62-0.65. Granule particle size was measured using sieve analysis for each drug layer blend. Granulation of all drug layers using the same processing parameters (Roll Speed=4.0 RPM, Roll Force=2.0 kN/cm, Roll Gap=2.0 mm, Mill Screen Size=1.0 mm) resulted in similar granule particle size distributions. The average particle size generally was between 75-850 μm with populations of particles having particle sizes between, for example, 75-106 μm (less than 5% mass fraction), 106-150 μm (about 10% mass fraction), 150-250 μm (about 15% mass fraction), 250-500 μm (about 30% mass fraction), and 500-850 μm (about 37% mass fraction).

Bilayer Tablet Compression

The final blends were compressed into fourteen tablet batches using a Korsch XM12 tablet press with process parameters summarized in Table 12. Four 12.0 mm SRC tooling stations were used to achieve a run time of between 10-20 min for each formulation. All 14 tablet batches were made successfully with average tablet weight, thickness, and hardness that ranged from 733.8-739.9 mg, 7.10-7.16 mm, and 14.0-16.3 kP, respectively. Average tablet weight, thickness, and hardness were within their acceptable ranges.

TABLE 12

Tablet Compression Parameters for Bilayer Tablets on Korsch XM12

| Parameter | Value |
|---|---|
| Tableting mode (single/bilayer) | Bilayer mode |
| Tooling sizes | 12.00 mm SRC (.4724") DIA. STD CUP |
| Tooling drawing number | 91558 |
| Number of tooling stations | 4 |
| Turret speed | 30 rpm |
| Drug layer weight | 491.8 mg |
| Swellable layer weight | 245.9 mg |
| Tablet core weight | 737.7 mg |
| Fill Cam | [10 mm] or as needed |
| First layer feed frame paddle type | Standard square paddle |
| First layer feed frame paddle speed | 65 rpm (adjust speed as needed; CW rotation) |
| Drug layer dosing depth | 8.00 mm |
| Drug layer insertion depth | 3.00 mm |
| Drug layer edge thickness | 4.83 mm |
| Second layer feed frame paddle type | 45° single bevel paddle (Korsch part number 80700345) |
| Second layer feed frame paddle speed | 55 rpm (adjust speed as needed; CW rotation) |

TABLE 12-continued

Tablet Compression Parameters for Bilayer Tablets on Korsch XM12

| Parameter | Value |
|---|---|
| Sweller layer dosing depth | 6.00 mm |
| Pre compression edge thickness | 4.83 mm (no pre-compression force) |
| Main compression edge thickness | 4.23 mm |
| Tablet hardness | 15 kP |
| Drug layer tamping forced | [1000N] (Adjust as needed-avg. tamp force not to exceed 1.3 kN) |
| Pre-compression force | 380 N |
| Compression force | 8.0 KN |
| Approximate tablet thickness | 7.2 mm (7.0 to 7.2 mm) |
| De-duster | Yes |

Coating Layer

Tablet Cores 1-14 were coated with one of Coating Compositions A-C shown in Table 13. The coating conditions are summarized in Table 14.

Tablet Cores 1-12 were coated with Coating Composition A, Tablet Core 13 was coated with Coating Composition B, and Tablet Core 14 was coated with Coating Composition C. The target coating wet weight gain was 7.5%.

TABLE 13

Coating Compositions A-C

| Ingredient (% w/w) | Coating Comp. A | Coating Comp. B | Coating Comp. C |
|---|---|---|---|
| CA | 4.00 | 4.05 | 3.95 |
| PEG 3350 | 1.00 | 0.95 | 1.05 |
| Acetone | 91 | 91 | 91 |
| Purified water | 4 | 4 | 4 |

TABLE 14

Coating Parameters for CA/PEG Coating of APR SCT Tablet Cores 1-14

| Process | Process Parameters | Target |
|---|---|---|
| Tablet Pre-heating | Air flow rate | 40 CFM |
| | $T_{in}$ | 45° C. |
| | $T_{out}$ | 35° C. |
| | Pan speed | 3 rpm jog (jog 5 sec on, 30 sec off) |
| CA/PEG Coating | Air-flow rate | 40 CFM |
| | $T_{out}$ | 35° C. |
| | Atomization air pressure | 10 psi |
| | Pattern air pressure | 5 psi |
| | Spray-solution feed rate per nozzle | 20 g/min |
| | Pan speed | 22 rpm (1.3 L pan) |
| | Gun-to-Bed Distance C | 2.5 in |
| | PLC Temperature control | Inlet |
| | Wet coating weight gain | 7.5 wt % |
| Jog Drying | Air-flow rate | 40 CFM |
| | $T_{out}$ | 35° C. |
| | $T_{in}$ | 45° C. |
| | Pan speed | 3 rpm jog (jog 5 sec on, 30 sec off) |

The coated tablets were drilled using the phase 1 laser drill with a 1.2 mm hole to provide the drug release orifice and subsequently pan dried for approximately 15 hours.

Dissolution Studies

Dissolution (n=6) was performed on the Tablets 6-10 each having a different drug layer (DL 1-5) and the same swellable layer (SL-6). The variation in composition and dissolution metrics for these formulations is presented in Table 15. The dissolution profiles for these formulations are shown in FIG. 1. No significant differences in dissolution were observed for the five formulations. The tablets provided suitable dissolution profiles.

TABLE 17

CA/PEG coatings of Tablet 5

| Tablet | DL | SL | CA:PEG ratio | RR[1] | $t_{50}$ (h) | Dose Delivered at 8 h (%) | Residual (%) | $t_{lag}$ (h) |
|---|---|---|---|---|---|---|---|---|
| 5A | DL-6 | SL-5 | 81:19 | 5.5 | 7.7 | 52.2 | 21.2 | 1.0 |
| 5 | DL-6 | SL-5 | 80:20 | 6.3 | 8.8 | 45.1 | 23.3 | 1.3 |
| 5B | DL-6 | SL-5 | 79:21 | 5.6 | 7.8 | 51.4 | 21.2 | 1.1 |

[1]zero-order release rate (RR) (5-10 h)

TABLE 15

Dissolution of Tablets 6-10

| Tablet[1] | DL | PEO 200 kDa | Mg Stearate (IG) | Mg Stearate (EG) | RR[2] | $t_{50}$ (h) | Dose Delivered at 8 h (%) | Residual (%) | $t_{lag}$ (h) |
|---|---|---|---|---|---|---|---|---|---|
| 6 | DL-1 | − | − | + | 5.3 | 8.2 | 49.3 | 23.2 | 1.0 |
| 7 | DL-2 | + | − | − | 6.0 | 9.5 | 41.1 | 22.8 | 1.2 |
| 8 | DL-3 | − | + | − | 5.7 | 9.0 | 44.7 | 25.0 | 1.2 |
| 9 | DL-4 | + | + | + | 5.7 | 7.9 | 50.8 | 22.3 | 1.0 |
| 10 | DL-5 | 0 | 0 | 0 | 6.1 | 8.2 | 48.6 | 23.7 | 1.2 |
| | + | 105% | 105% | 105% | | | | | |
| | − | 95% | 95% | 95% | | | | | |
| | 0 | 0 | 0 | 0 | | | | | |

[1]all tablets prepared with swellable layer SL-6
[2]zero-order release rate (RR) (5-10 h)

Figure 2:
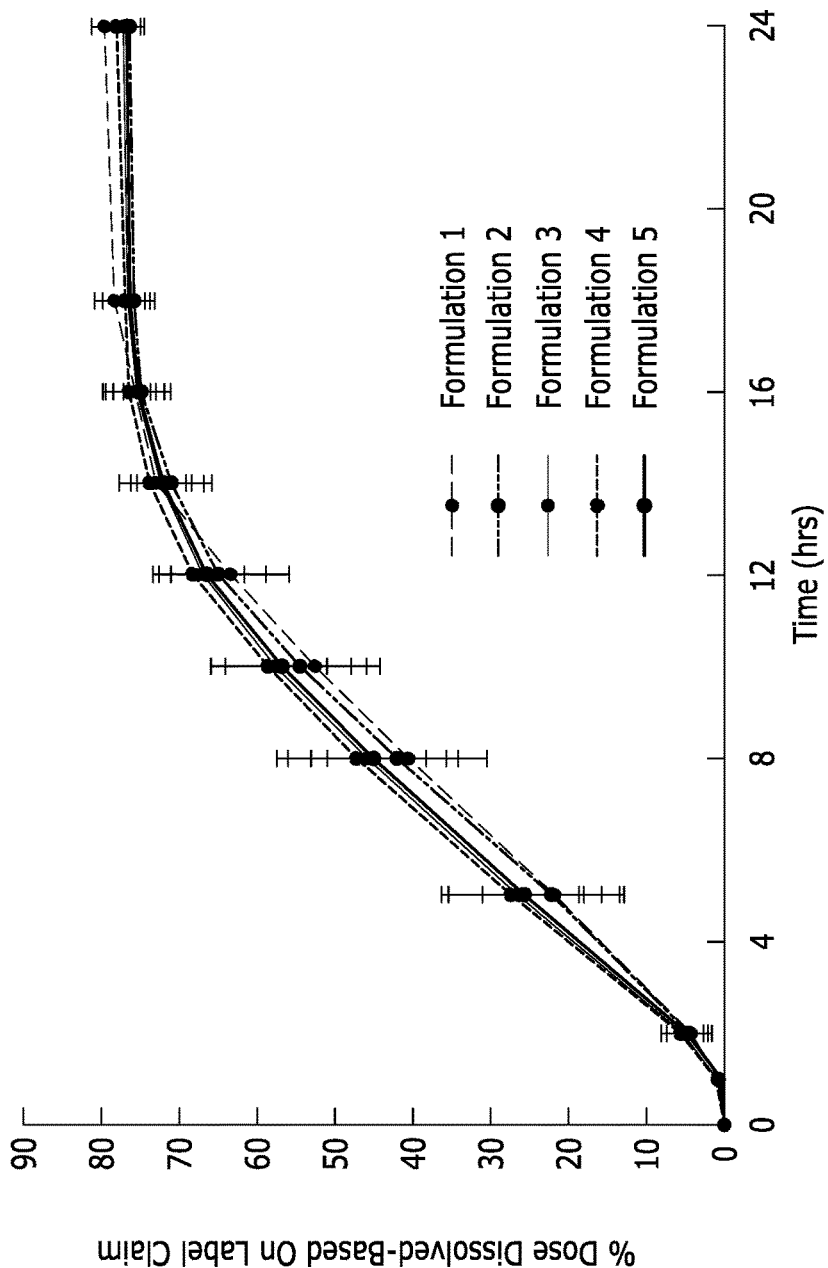
FIG. 2 shows dissolution profiles of Tablets 1-5.

Dissolution (n=6) was performed on the Tablets 1-5 each having a different swellable layer (SL 1-5) and the same drug layer (DL-6). The variation in excipient amounts and key dissolution metrics is presented in Table 16. The dissolution profiles are shown in FIG. 2. No significant difference in dissolution profile was observed for the five formulations. The tablets provided suitable dissolution profiles.

TABLE 16

Dissolution of Tablets 1-5

| Tablet[1] | SL | PEO 5000 kDa | Mg Stearate (IG) | Mg Stearate (EG) | RR[2] | $t_{50}$ (h) | Dose Delivered at 8 h (%) | Residual (%) | $t_{lag}$ (h) |
|---|---|---|---|---|---|---|---|---|---|
| 1 | SL-1 | − | − | + | 6.2 | 9.5 | 40.9 | 20.4 | 1.4 |
| 2 | SL-2 | + | − | − | 6.5 | 9.3 | 41.9 | 22.0 | 1.3 |
| 3 | SL-3 | − | + | − | 6.3 | 8.5 | 46.7 | 22.9 | 1.3 |
| 4 | SL-4 | + | + | + | 6.3 | 8.5 | 47.4 | 21.9 | 1.2 |
| 5 | SL-5 | 0 | 0 | 0 | 6.3 | 8.8 | 45.1 | 23.3 | 1.3 |
| | + | 105% | 105% | 105% | | | | | |
| | − | 95% | 95% | 95% | | | | | |
| | 0 | 0 | 0 | 0 | | | | | |

[1]all tablets prepared with drug layer DL-6
[2]zero-order release rate (RR) (5-10 h)

Figure 3:
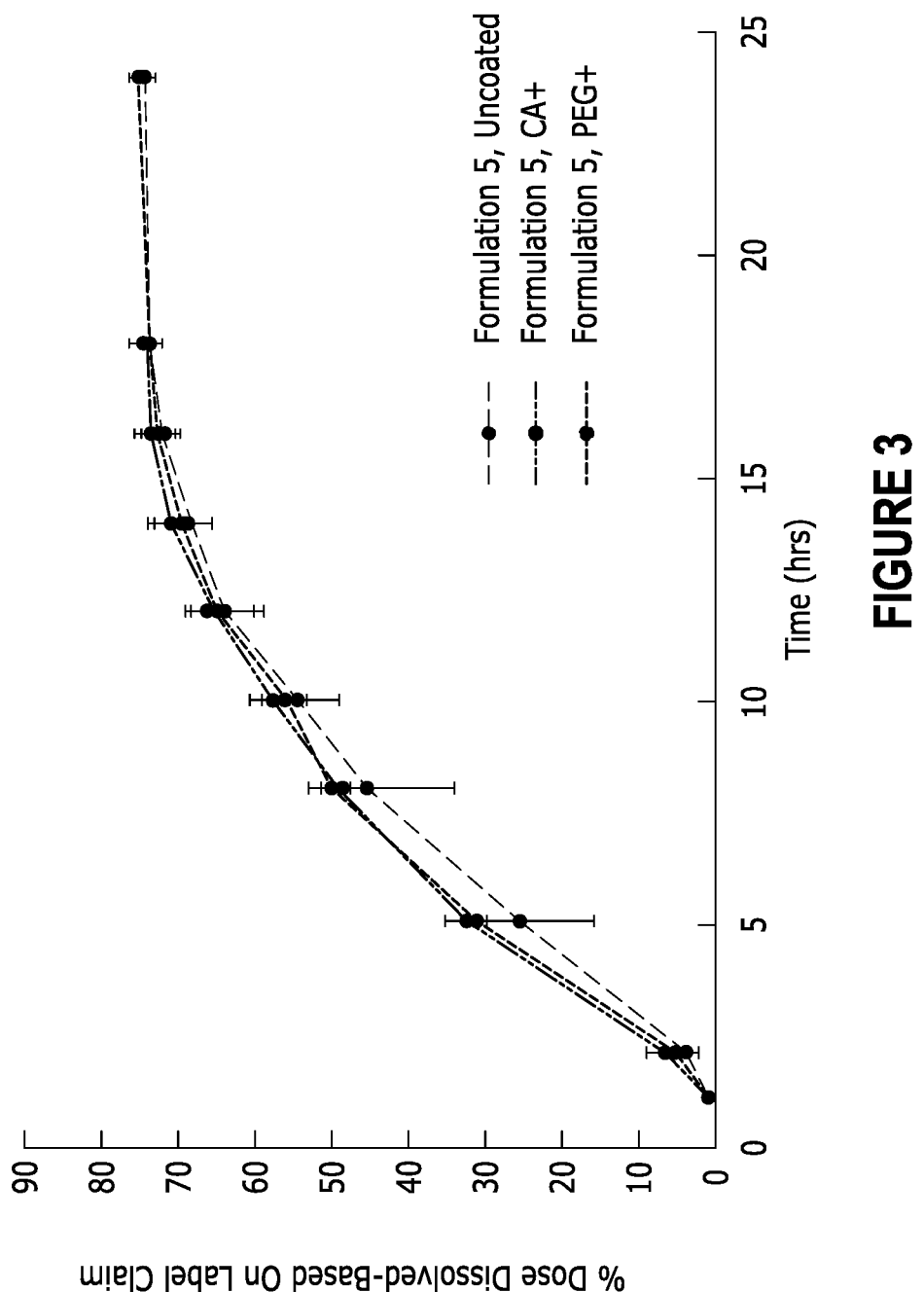
FIG. 3 shows dissolution profiles of tablet core 5 uncoated or with a CA or PEG coating.

Tablet 5 was coated with three different coating solution compositions by varying the ratio of cellulose acetate and polyethylene glycol (PEG 3350) to provide Tablets 5, 5A, and 5B. The specific ratios tested as well as key dissolution metrics can be found in Table 17. The dissolution profiles are shown in FIG. 3. There was no observed difference in the dissolution profile for the three formulations.

Figure 4:
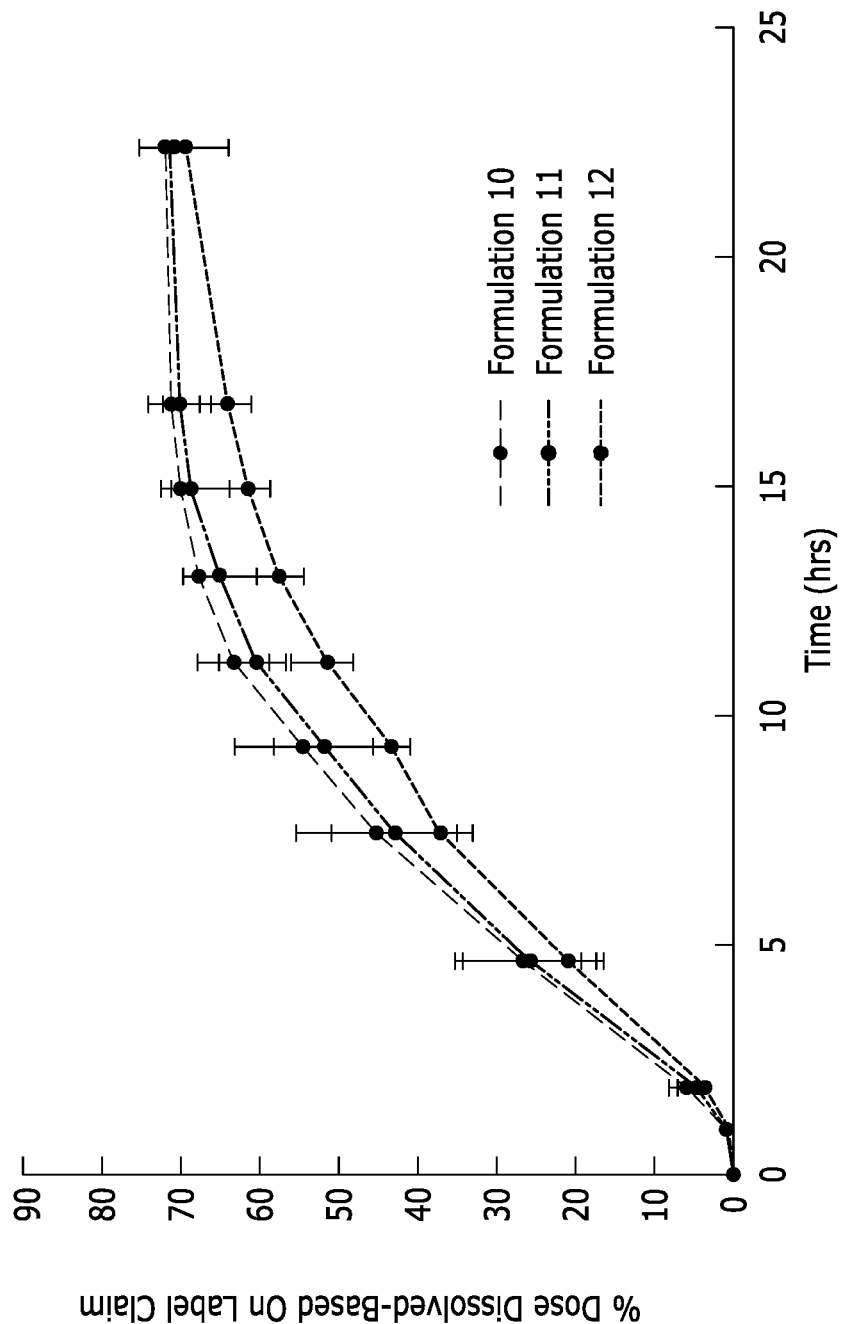
FIG. 4 shows dissolution profiles of Tablets 10-12.

Tablets 10-12 were made with SDD that had varying levels of apremilast to HPMCAS-L as outlined in Table 18, which also includes the key dissolution metrics from the study. The dissolution profiles are presented in FIG. 4. A slower release profile with a slight increase in residuals was observed for the formulation containing SDD with an increased amount of apremilast (52%) relative to the centerline SDD (50% apremilast). For this analysis, the dose per tablet for these formulations was not normalized to the actual amounts found in their respective SDD lots, and centerline dose was assumed.

TABLE 18

Dissolution Results for Tablets 10-12

| Tablet | DL | SL | APR:HPMCAS-L Ratio in SDD | RR[1] | $t_{50}$ (h) | Dose Delivered at 8 h (%) | Residual (%) | $t_{lag}$ (h) |
|---|---|---|---|---|---|---|---|---|
| 10 | DL-5 | SL-6 | 50:50 | 6.1 | 8.2 | 48.6 | 23.7 | 1.2 |
| 11 | DL-7 | SL-6 | 48:52 | 5.4 | 8.8 | 46.1 | 23.6 | 1.0 |
| 12 | DL-8 | SL-6 | 52:48 | 4.9 | 10.8 | 39.9 | 26.2 | 1.3 |

[1]zero-order release rate (RR) (5-10 h)

Example 3

This example demonstrates oral dosage forms in accordance with embodiments of the disclosure.

Eight tablets (Tablets 15-22) were prepared as described herein containing the components set forth in Table 19. The drug layers of each of the tablets comprised apremilast and HPMCAS in weight ratio of 50:50. Further, the drug layer of Tablet 15 further comprised extragranular mannitol as a diluent. In addition, Dosage Forms 21 and 22 further comprised a sub-coat layer comprising hydroxypropyl methylcellulose.

TABLE 19

Tablets 15-22

| Component | 15 | 16 | 17 | 18 | 19 | 20 | 21 | 22 |
|---|---|---|---|---|---|---|---|---|
| | | | | (mg/tablet) | | | | |
| DRUG LAYER | | | | | | | | |
| Intragranular | | | | | | | | |
| Apremilast (mg) | 75.0 | 60.0 | 60.0 | 65.0 | 65.0 | 70.0 | 75.0 | 75.0 |
| HPMCAS (mg) | 75.0 | 60.0 | 60.0 | 65.0 | 65.0 | 70.0 | 75.0 | 75.0 |
| PEO 200 kDa (mg) | 314.8 | 307.2 | 307.2 | 332.8 | 332.8 | 358.4 | 314.8 | 314.8 |
| Mannitol (mg) | 12.3 | 48.0 | 48.0 | 52.0 | 52.0 | 56.0 | 22.1 | 22.1 |
| Mg stearate (mg) | 1.2 | 1.2 | 1.2 | 1.3 | 1.3 | 1.4 | 1.2 | 1.2 |
| Extra-granular | | | | | | | | |
| cSiO₂ (mg) | 2.5 | 2.4 | 2.4 | 2.6 | 2.6 | 2.8 | 2.5 | 2.5 |
| Mannitol (mg) | 9.8 | — | — | — | — | — | — | — |
| Mg stearate (mg) | 1.2 | 1.2 | 1.2 | 1.3 | 1.3 | 1.4 | 1.2 | 1.2 |
| SWELLABLE LAYER | | | | | | | | |
| PEO 5000 kDa (mg) | 159.6 | 155.8 | 155.8 | 168.7 | 168.7 | 181.7 | 159.6 | 159.6 |
| MCC (mg) | 63.4 | 61.9 | 61.9 | 67.1 | 67.1 | 72.3 | 63.4 | 63.4 |
| NaCl (mg) | 21.1 | 20.6 | 20.6 | 22.4 | 22.4 | 24.1 | 21.1 | 21.1 |
| Iron oxide red (mg) | 0.5 | 0.5 | 0.5 | 0.5 | 0.5 | 0.5 | 0.5 | 0.5 |
| Mg stearate (mg) | 1.2 | 1.2 | 1.2 | 1.3 | 1.3 | 1.4 | 1.2 | 1.2 |
| Core Tablet Total wt (mg) | 737.7 | 720.0 | 720.0 | 780.0 | 780.0 | 840.0 | 737.7 | 737.7 |

TABLE 19-continued

Tablets 15-22

| Component | 15 | 16 | 17 | 18 | 19 | 20 | 21 | 22 |
|---|---|---|---|---|---|---|---|---|
| | | | | (mg/tablet) | | | | |
| COATING LAYER | | | | | | | | |
| HPMC (mg) | — | — | — | — | — | — | 18.4 | 18.4 |
| Purified water* | | | | | | | | |
| Film-coated tablet Total wt. (mg) | — | — | — | — | — | — | 756.1 | 756.1 |
| CA (mg) | 41.3 | 37.4 | 72.0 | 37.4 | 74.9 | 40.3 | 36.3 | 49.6 |
| PEG (mg) | 10.3 | 9.4 | 18.0 | 9.4 | 18.7 | 10.1 | 9.1 | 12.4 |
| Acetone* | — | — | — | — | — | — | — | — |
| Purified water* | | | | | | | | |
| CA coated tablet Total wt. (mg) | 789.2 | 766.8 | 810 | 826.8 | 873.6 | 890.4 | 756.1 | 756.1 |
| Opadry pink (mg) | 27.6 | — | — | — | — | — | — | — |
| Purified water* | | | | | | | | |
| Tablet Total wt. (mg) | 816.8 | 766.8 | 810 | 826.8 | 873.6 | 890.4 | 801.5 | 818.1 |

*removed during processing

Subjects were administered one of Tablets 16-22 in fed state (e.g., 30 minutes after consuming a moderate- or high-fat meal).

TABLE 20

Tablets 16-22

| Tablet | Drug Loading (SDD[1])% | Coating level (CA:PEG)% | Relative AUC∞ (%)[1] | Relative $C_{max}$ (%)[2] |
|---|---|---|---|---|
| | Single day dosing (fasted) | | | |
| 16 | 16.7 | 6.5 | 77.4 | 93.2 |
| 17 | 16.7 | 12.5 | 66.1 | 68.7 |
| 18 | 16.7 | 6.0 | 90.1 | 91.4 |
| 19 | 16.7 | 12.0 | 58.8 | 64.3 |

TABLE 20-continued

Tablets 16-22

| Tablet | Drug Loading (SDD[1])% | Coating level (CA:PEG)% | Relative AUC∞ (%)[3] | Relative $C_{max}$ (%)[2] |
|---|---|---|---|---|
| 20 | 16.7 | 6.0 | 73.1 | 99.3 |
| 21 | 20.3 | 6.1 | 66.6 | 91.7 |
| 22 | 20.3 | 8.4 | 80.2 | 91.6 |
| Single day dosing (standard meal) | | | | |
| 21 | 20.3 | 6.1 | 943 | 108.9 |
| Multiple Doses for 14 days (moderate-fat meal) | | | | |
| 20 | 16.7 | 6.0 | 80.23 | 89.8 |
| 21 | 20.3 | 6.1 | 88.83 | 93.4 |
| 22 | 20.3 | 8.4 | 125.33 | 127.4 |

[1]SDD: APR:HPMCAS 1:1
[2]Ratio(%) of adjusted geometric means (test/IR BID)
[3]$AUC_{0-24}$ Example 4

This example demonstrates oral dosage forms in accordance with embodiments of the disclosure.

Two 75 mg SCT QD apremilast tablets of Formulation 15 were prepared (Tablets A and B). Subjects were administered Tablet A (Treatment A) and Tablet B (Treatment B) during the study. Treatments were administered with approximately 240 mL (or 8 oz) of non-carbonated, room-temperature water. Subjects underwent an overnight fast of at least 10 hours prior to each dosing period and for at least 4 hours after the morning dose. No food or beverages (excluding water) were allowed for at least 4 hours postdose. Water was allowed as desired except for 1 hour prior to dosing and 1 hour postdose.

Figure 5:
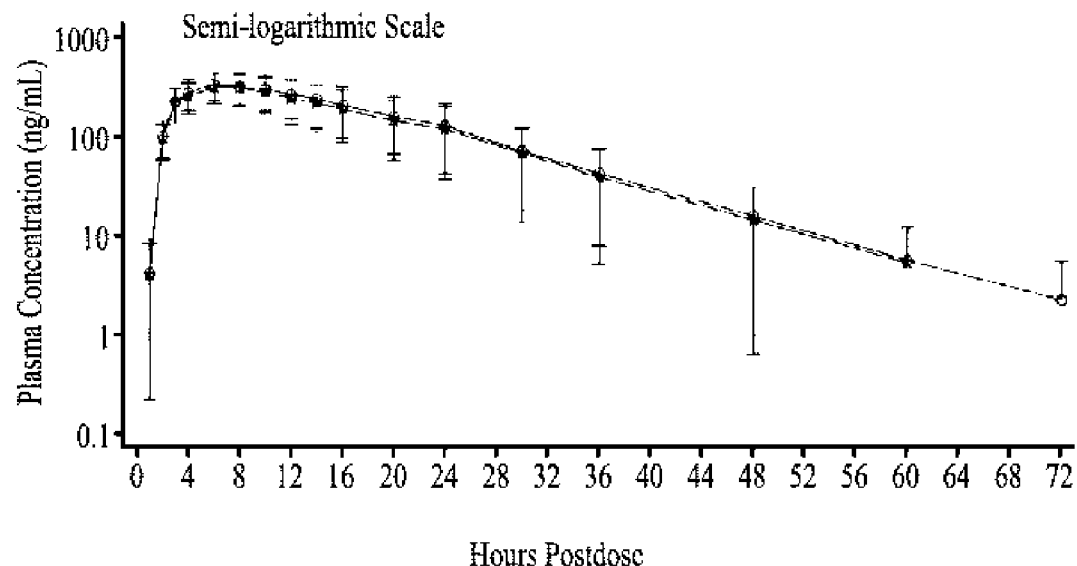
FIG. 5 shows Mean (±SD) Apremilast Plasma Concentrations—Time Profiles.

Blood samples were collected at specified time points for pharmacokinetic (PK) and clinical laboratory assessments. Safety was monitored throughout the study. Mean (±SD) apremilast plasma concentrations versus time profiles is presented in FIG. 5. All pharmacokinetic estimates were calculated using actual recorded blood drawing time. Plasma pharmacokinetic parameters by treatment are summarized in Table 21.

TABLE 21

Geometric Mean (Geometric CV %) Estimates of Apremilast PK Parameters

| Parameter | Treatment A | Treatment B |
|---|---|---|
| $AUC_{0-t}$ (h*ng/ml) | 6040 (53.5) | 5650 (55.2) |
| $AUC_{0-\infty}$ (h*ng/mL) | 6080 (53.5) | 5680 (55.2) |
| $C_{max}$ (ng/ml) | 382 (28.1) | 357 (28.2) |
| $t_{1/2}$ (h) | 7.2 (29.7) | 7.0 (25.6) |
| $T_{max}$ (h)$^a$ | 6.0 (3.0-14.0) | 8.0 (3.0-14.0) |
| $t_{lag}$ (h)$^a$ | 0.50 (0.00, 1.00) | 0.50 (0.50, 1.00) |
| CL/F (L/h) | 12.3 (53.5) | 13.2 (55.2) |
| $V_z/F$ (L) | 128 (49.8) | 134 (47.4) |

Following a single oral dose administration of apremilast 75 mg SCT formulation (Treatment A or Treatment B), apremilast was slowly absorbed with maximum plasma concentrations occurring at a median time to maximum plasma concentration ($T_{max}$) approximately at 6 and 8 hours respectively. The exposures of Treatment B are slightly lower but considered comparable to those observed in Treatment A ($C_{max}$: 357 ng/mL vs. 382 ng/mL, $AUC_{0-t}$:5650 h*ng/mL vs. 6040 h*ng/mL, and $AUC_{0-\infty}$: 5680 h*ng/mL vs. 6080 h*ng/mL). After achieving $C_{max}$, the apremilast concentrations declined with terminal elimination half-life ($t_{1/2}$) of approximately 7 hours for both Treatment A and Treatment B.

Example 5

This example demonstrates oral dosage forms in accordance with embodiments of the disclosure.

Subjects were administered Tablet 21 once-daily during the study and compared with a 30 mg IR apremilast formulation and a 75 mg gastroretentive (GR) formulation. Treatments were administered with approximately 240 mL (or 8 oz) non-carbonated, room-temperature water. On dosing days, subjects were fasted for at least 8 hours prior to each morning meal and for at least 4 hours after the morning dose. During fasting periods, water was allowed ad libitum except from between 1 hour prior to dosing and 1 hour postdose (excluding any water given with IP). A standard meal was administered 30 minutes prior to administration of the morning dose. The standard meal consisted of approximately 450 calories, 25% of the calories from fat. The standard meal content was equivalent to 8 oz of 1% fat milk, one large hard-boiled egg, two slices of whole grain toast, one pat of butter (5 g), and one medium banana. The content (with regard to calories, fat, protein, and carbohydrates) and timing of lunch, dinner, and all snacks was consistent across all periods on all dosing days. Lunch, dinner, and a snack were provided approximately 4, 9, and 13 hours after the morning dose, respectively.

Blood samples were collected at specified time points for pharmacokinetic (PK) and clinical laboratory assessments. Safety was monitored throughout the study. Mean (±SD) apremilast plasma concentrations versus time profiles for both Day 1 and Day 5 are presented in FIGS. 6 and 7, respectively. All pharmacokinetic estimates were calculated using actual recorded blood drawing time. Plasma pharmacokinetic parameters for all subjects who completed the treatments are presented are summarized in Table 22.

TABLE 22

Geometric Mean (Geometric CV %) Estimates of Apremilast Pharmacokinetic Parameters

| Day | Parameter | 30 mg IR BID | Tablet 21 | 75 mg GR Tablet |
|---|---|---|---|---|
| Day 1 | $AUC_{0-24}$ (ng·h/mL) | 4090 (26.9) | 4190 (30.2) | 3620 (27.4) |
| | $AUC_{0-t}$ (ng·h/mL) | 4080 (26.9) | 4180 (30.1) | 3610 (27.4) |
| | $C_{max}$ (ng/ml) | 351 (28.4) | 358 (27.6) | 406 (31.2) |
| | $T_{max}$ (h)$^a$ | 3.00 (2.00, 5.00) | 6.00 (4.00, 11.80) | 6.00 (4.00, 11.80) |
| | $t_{lag}$ (h) | 0.5 (0.0) | 0.89 (46.8) | 0.58 (28.3) |
| Day 5 | $AUC_{0-24}$ (ng·h/mL) | 5040 (29.9) | 5110 (34.1) | 4010 (33.1) |
| | $AUC_{0-t}$ (ng·h/mL) | 6150 (31.7) | 5980 (38.1) | 5270 (40.5) |
| | $AUC_{0-\infty}$ (ng·h/mL) | 6210 (31.2) | 6020 (38.2) | 5410 (42.8) |
| | $C_{max}$ (ng/ml) | 436 (24.9) | 398 (30.9) | 448 (36.4) |
| | $T_{max}$ (h)$^a$ | 2.00 (1.00, 5.00) | 6.00 (3.02, 8.00) | 6.00 (3.00, 24.00) |
| | $t_{lag}$ (h)$^b$ | NA | NA | NA |
| | $t_{1/2}$ (h) | 8.11 (28.6) | 7.13 (32.0) | 10.4 (48.8) |
| | CL/F (L/h) | 11.0 (26.8) | 14.7 (34.1) | 18.7 (33.1) |
| | $V_z/F$ (L) | 129 (38.6) | 151 (30.9) | 280 (47.4) |
| | $F_{rel1}$ (%) | NA | 96.9 (17.2) | 87.2 (36.1) |
| | $F_{rel2}$ (%) | NA | 77.5 (17.2) | 69.8 (36.1) |
| | RA | 1.23 (11.0) | 1.22 (21.0) | 1.11 (36.7) |

Figure 6:
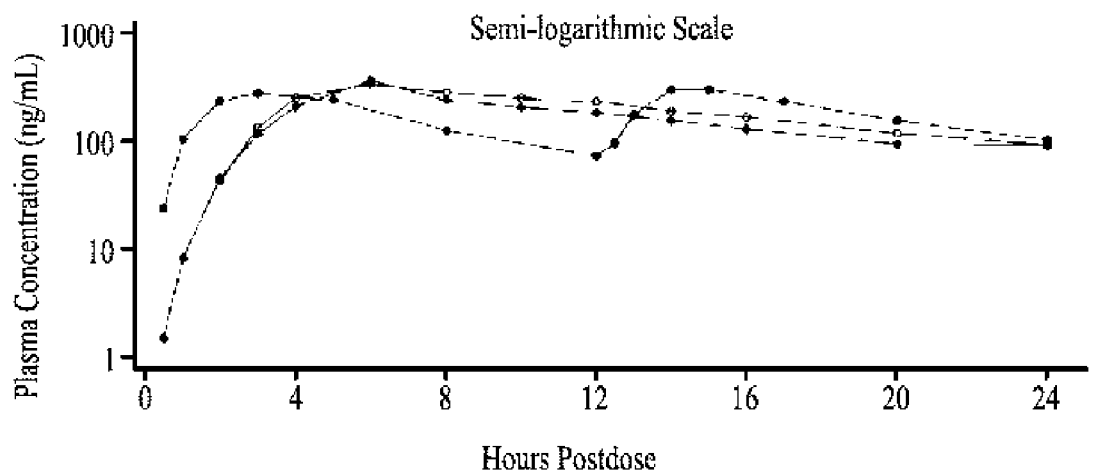
FIG. 6 shows apremilast plasma concentrations over 24 hours of 75 mg Tablet 21 once a day (open circles), compared to a 30 mg immediate release formulation twice a day (filled circles) and 75 mg gastrorentive (GR) tablet once a day (filled diamonds).
Figure 7:
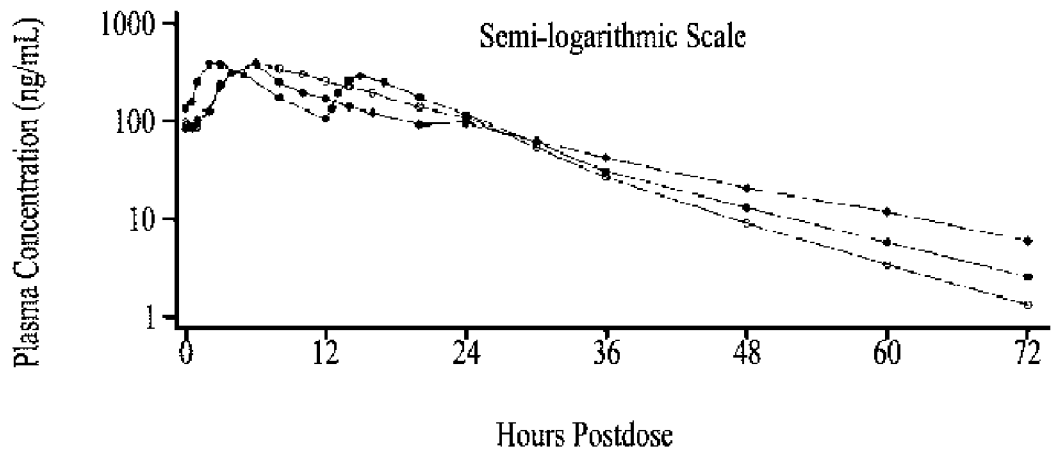
FIG. 7 shows apremilast plasma concentrations over 5 days of 75 mg Tablet 21 once a day (open circles), compared to a 30 mg immediate release formulation twice a day (filled circles) and 75 mg gastrorentive (GR) tablet once a day (filled diamonds).

Apremilast was slowly absorbed with maximum plasma concentrations occurring at a median time to maximum plasma concentration ($T_{max}$) of approximately 6 hours when Tablet 21 was orally administered as a single dose and multiple doses once daily (FIG. 6, FIG. 7, and Table 22). The peak plasma concentrations of apremilast ($C_{max}$) were similar on Day 1 between Tablet 21 and 30 mg IR BID, but $C_{max}$ was slightly lower for Table 21 on Day 5. Table 21 exhibited a delayed median time to reach $C_{max}$ compared to 30 mg IR BID (2 hours postdose) and a relatively lower $C_{max}$ based on the 75 mg daily dose, reflecting a sustained release effect of a typical modified release formulation (FIG. 6, FIG. 7, and Table 22).

After achieving steady-state $C_{max}$ on Day 5, apremilast concentration declined with terminal elimination half-life ($t_{1/2}$) of approximately 7 hours following administration of Tablet 21. The $t_{1/2}$ of apremilast was similar between Tablet 21 and 30 mg IR BID in healthy male subjects following multiple doses. $AUC_{0-24}$, $AUC_{0-t}$, and $AUC_{0-\infty}$ were similar between Tablet 21 and 30 mg IR BID following single and multiple oral administration. The accumulation ratio of Table 21 was also similar to that of 30 mg IR BID following multiple oral doses. $C_{trough}$ on Day 5 following oral administration of Tablet 21 was lower relative to that for 30 mg IR BID. Relative bioavailability was comparable between Tablet 21 and 30 mg IR BID, but the dose-normalized relative bioavailability of Tablet 21 was approximately 23% lower than that of 30 mg IR BID.

Apremilast was slowly absorbed with maximum plasma concentrations occurring at a median time to maximum plasma concentration ($T_{max}$) of approximately 6 hours when 75 mg GR Tablet was orally administered as a single and multiple doses (FIG. 6, FIG. 7, and Table 22). The peak plasma concentrations of apremilast ($C_{max}$) for 75 mg GR Tablet were higher than the $C_{max}$ for IR. 75 mg GR Tablet exhibited a delayed median time to reach $C_{max}$ compared to IR (2 h postdose) and a relatively lower $C_{max}$ based on the 75 mg daily dose, reflecting a sustained release effect of a typical modified release formulation (FIG. 6, FIG. 7, and Table 22).

After achieving steady-state $C_{max}$ on Day 5, apremilast concentration declined with terminal elimination half-life ($t_{1/2}$) of approximately 10 hours following administration of 75 mg GR Tablet. The $t_{1/2}$ of apremilast was 2 to 3 hours longer for 75 mg GR Tablet compared to 30 mg IR BID in healthy male subjects following multiple doses. $AUC_{0-24}$, $AUC_{0-t}$, and $AUC_{0-\infty}$, were generally lower for 75 mg GR Tablet compared to 30 mg IR BID following single and multiple oral administration. The accumulation ratio and Day 5 $C_{trough}$ for dosing 75 mg GR Tablet were less compared to 30 mg IR BID following multiple oral doses (Table 22). Both relative bioavailability and the dose-normalized relative bioavailability of 75 mg GR Tablet were lower than those for 30 mg IR BID.

The results of the statistical analyses for $AUC_{0-24}$, $C_{max}$, and $C_{trough}$ for both the bioavailability of Tablet 21 apremilast QD formulation (test) and 75 mg GR Tablet apremilast QD formulation (test), relative to the 30 mg IR BID apremilast formulation (reference) are summarized in Table 23. Day 1 and Day 5 median difference analyses of $T_{max}$ are summarized in Table 24.

TABLE 23

Comparison of Apremilast PK Parameters Relating Exposure After Tablet 21 & GR Tablet

| Parameter | Treatment | Geometric Mean | Comparison | Ratio (%) of Geometric Means | 90% Cl of Ratio of Geometric Means (%) | Intra-subject Variability CV % |
|---|---|---|---|---|---|---|
| $AUC_{0-24}$ (ng · h/mL) | Tablet 21 | 5068.4 | 21 vs IR | 100.8 | (90.2, 112.6) | 19.8 |
| | GR | 3953.5 | GR vs IR | 78.6 | (70.3, 87.9) | |
| | IR | 5029.0 | | | | |
| $C_{max}$ (ng/mL) | Tablet 21 | 399.4 | 21 vs IR | 91.4 | (78.2, 106.8) | 28.1 |
| | GR | 448.9 | GR vs IR | 102.7 | (87.9, 120.1) | |
| | IR | 437.0 | | | | |
| $C_{trough}$ (ng/mL) | Tablet 21 | 81.0 | 21 vs IR | 64.1 | (52.1, 78.9) | 38.0 |
| | GR | 75.8 | GR vs IR | 60.0 | (48.7, 74.0) | |
| | IR | 126.3 | | | | |

TABLE 24

Comparison of $T_{max}$ of Tablet 21 & GR Tablet

| Day | Parameter | Treatment | Median | Comparison | Median Difference | 90% Cl of Median Difference | p-value |
|---|---|---|---|---|---|---|---|
| 1 | $T_{max}$ (h) | Tablet 21 | 6.02 | B vs A | 3.50 | (2.01, 4.50) | <0.0001 |
| | | GR | 6.00 | C vs A | 2.50 | (2.00, 3.50) | <0.0001 |
| | | IR | 3.00 | | | | |
| 5 | $T_{max}$ (h) | Tablet 21 | 6.00 | B vs A | 3.00 | (2.50, 4.00) | <0.0001 |
| | | GR | 5.00 | C vs A | 2.50 | (2.00, 3.50) | <0.0001 |
| | | IR | 2.50 | | | | |

Following 5-day multiple oral doses of Tablet 21 and GR Tablet once daily, Day 5 $AUC_{0-24}$ values were approximately 100% and 79% of the reference $AUC_{0-24}$ value, respectively. Day 5 $C_{max}$ for Tablet 21, and GR Tablet were 91% and 103% of the reference formulation IR 30 mg BID, respectively (Table 23).

The $AUC_{0-24}$ is considered to be equivalent between the Tablet 21 apremilast QD formulation and the 30 mg IR apremilast BID formulation since the 90% CI of the ratio of $AUC_{0-24}$ geometric means shown in Table 23 was within the limits of 80% to 125%, the conventional bioequivalent criteria. The $C_{max}$ and $C_{trough}$ though were approximately 9% and 36% lower, respectively.

The $AUC_{0-24}$ for GR Tablet was approximately 21% lower compared to 30 mg IR BID. However, the $C_{max}$ was considered to be equivalent between the 75 mg GR Tablet apremilast QD formulation and the 30 mg IR apremilast BID formulation since the 90% CI of the ratio of $C_{max}$ geometric mean shown in Table 23 was within the limits of 80% to 125%, the conventional bioequivalent criteria. The $C_{trough}$ for GR Tablet was approximately 40% lower compared to that for 30 mg IR BID.

The median $T_{max}$ analyses are shown in Table 24. Both median values of $T_{max}$ of the Tablet 21 apremilast QD formulation and the 75 mg GR Tablet apremilast QD formulation were significantly delayed with median difference from 2.5 hours to 3 hours when compared to 30 mg IR apremilast BID formulation. The median difference in $T_{max}$ for both test formulations compared to reference formulation were statistically significant ($p<0.0001$).

Example 6

This example demonstrates tablet formulations and oral dosage forms of embodiments of the disclosure. Tablet formulations 6-1 to 6-13 were prepared comprising the components set forth in Table 25.

TABLE 25

Core Tablet Formulations and Oral Dosage Forms of the Disclosure.

| Component | Tablet (mg/tablet) | | | | | | | | | | | | |
|---|---|---|---|---|---|---|---|---|---|---|---|---|---|
| | 6-1 | 6-2 | 6-3 | 6-4 | 6-5 | 6-6 | 6-7 | 6-8 | 6-9 | 6-10 | 6-11 | 6-12 | 6-13 |
| DRUG LAYER | | | | | | | | | | | | | |
| *Intragranular* | | | | | | | | | | | | | |
| Apremilast | 100 | 100 | 75 | 75 | 75 | 75 | 55 | 55 | 27.5 | 27.5 | 75 | 55 | 27.5 |
| HPMCAS) | 100 | 100 | 75 | 75 | 75 | 75 | 55 | 55 | 27.5 | 27.5 | 75 | 55 | 27.5 |
| PEO (300 kDa) | 150.7 | 274.6 | 113 | 206 | 274.6 | 274.6 | 82.9 | 151.1 | 41.4 | 75.5 | — | — | — |
| PEO (200 kDa) | 150.7 | — | 113 | — | — | — | 82.9 | — | 41.4 | — | 314.8 | 230.9 | 115.6 |
| NaCl | 26.7 | 53.3 | 20 | 40 | 40 | 40 | 14.7 | 29.3 | 7.3 | 14.7 | — | — | — |
| Mannitol | — | — | — | — | — | 25 | — | — | — | — | 12.3 | 9 | 4.5 |
| Mg stearate | 1.3 | 1.3 | 1 | 1 | 1 | 1 | 0.7 | 0.7 | 0.4 | 0.4 | 1.2 | 0.9 | 0.5 |
| *Extragranular* | | | | | | | | | | | | | |
| cSiO$_2$ | 2.7 | 2.7 | 2 | 2 | 2 | 2 | 1.5 | 1.5 | 0.7 | 0.7 | 2.5 | 1.8 | 0.9 |
| Mannitol | — | — | — | — | 50 | 25 | — | — | — | — | 9.8 | 7.2 | 3.6 |
| Mg stearate | 1.3 | 1.3 | 1 | 1 | 1 | 1 | 0.7 | 0.7 | 0.4 | 0.4 | 1.2 | 0.8 | 0.5 |
| SWELLABLE LAYER | | | | | | | | | | | | | |
| PEO (5000 kDa) | 173.1 | 173.1 | 129.8 | 129.8 | 173.1 | 173.1 | 95.2 | 95.2 | 47.6 | 47.6 | 159.6 | 117 | 58.6 |
| MCC | 68.8 | 68.8 | 51.6 | 51.6 | 68.8 | 68.8 | 37.8 | 37.8 | 18.9 | 18.9 | 63.4 | 46.5 | 23.3 |
| NaCl | 22.9 | 22.9 | 17.2 | 17.2 | 22.9 | 22.9 | 12.6 | 12.6 | 6.3 | 6.3 | 21.1 | 15.5 | 7.8 |
| Iron oxide red | 0.5 | 0.5 | 0.4 | 0.4 | 0.5 | 0.5 | 0.3 | 0.3 | 0.1 | 0.1 | 0.5 | 0.4 | 0.2 |
| Mg stearate | 1.3 | 1.3 | 1 | 1 | 1.3 | 1.3 | 0.7 | 0.7 | 0.4 | 0.4 | 1.2 | 0.9 | 0.5 |
| Core Tablet | 800.0 | 799.8 | 600.0 | 600.0 | 785.2 | 785.2 | 440.0 | 439.9 | 219.9 | 220.0 | 737.6 | 540.9 | 271.0 |
| COATING LAYER | | | | | | | | | | | | | |
| CA | 41.6 | 37.8 | 36.0 | 36.0 | 47.1 | 47.1 | 26.4 | 26.4 | 13.2 | 13.2 | 41.3 | 30.3 | 15.2 |
| PEG | 10.4 | 9.4 | 9.0 | 9.0 | 11.8 | 11.8 | 6.6 | 6.6 | 3.3 | 3.3 | 10.3 | 7.6 | 3.8 |
| Acetone* | | | | | | | | | | | | | |
| Purified water* | | | | | | | | | | | | | |
| CA coated tablet Total wt. (mg) | 852.0 | 847.0 | 645.0 | 645.0 | 844.1 | 844.1 | 473.0 | 472.9 | 236.4 | 236.5 | 789.2 | 578.8 | 290.0 |
| Opadry pink | — | — | — | — | — | — | — | — | — | — | 27.6 | 20.2 | 10.1 |
| Purified water* | | | | | | | | | | | | | |
| Tablet Total wt. (mg) | 852.0 | 847.0 | 645.0 | 645.0 | 844.1 | 844.1 | 473.0 | 472.9 | 236.4 | 236.5 | 816.8 | 599.0 | 300.1 |

Example 7

This example demonstrates 100 mg core tablet formulations of embodiments of the disclosure. 100 mg core tablet formulations 7-1 through 7-6 were prepared comprising the drug layer components set forth in Table 26. Each of 7-1 through 7-6 comprised the same swellable layer comprising the following components (wt % of swellable layer): 64.9% PEO, 25.8% MCC, 8.6% NaCl, 0.2% iron oxide red; and 0.5% Mg stearate. Each drug layer in 7-1 through 7-6 had a total weight of 533.3 mg and the swellable layer had a weight 266.7 mg providing for a total, uncoated weight of 800 mg for each tablet core composition.

TABLE 26

Core Tablet Compositions 7-1 through 7-6 (100 mg)

| | Core Tablet Comp. | | | | | |
|---|---|---|---|---|---|---|
| | 7-1 | 7-2 | 7-3 | 7-4 | 7-5 | 7-6 |
| Component | Drug Layer Intragranular (% blend) | | | | | |
| 50% APM:HPMCAS-L SDD | 37.5 | 37.5 | 37.5 | 37.5 | 37.5 | 37.5 |
| PEO (200 kDa) | 61.50 | 30.75 | — | 51.50 | 25.75 | — |
| PEO (600 kDa) | — | 30.75 | 61.50 | — | 25.75 | 51.50 |
| NaCl | — | — | — | 10.0 | 10.0 | 10.0 |
| Mg stearate | 0.25 | 0.25 | 0.25 | 0.25 | 0.25 | 0.25 |
| Component | Extragranular (% blend) | | | | | |
| cSiO$_2$ | 0.50 | 0.50 | 0.50 | 0.50 | 0.50 | 0.50 |
| Mg stearate | 0.25 | 0.25 | 0.25 | 0.25 | 0.25 | 0.25 |

The dissolution of core tablet formulations 7-1 through 7-6 was analyzed under the following conditions: Apparatus used: USP Apparatus 2 (Paddles); Vessel: 1 L dissolution vessel with low evaporation lids; Paddle stirring speed: 75±2 rpm; Dissolution medium temperature: 37.0±0.5° C.; Sample size: one tablet per vessel; Dissolution medium composition: 0.5% Tween® 80 in sodium acetate buffer, pH 5.5; Dissolution medium volume: 900 mL; Sample volume: 1.5 mL (auto-sampler) or 5 mL (manual sampling).

Figure 8:
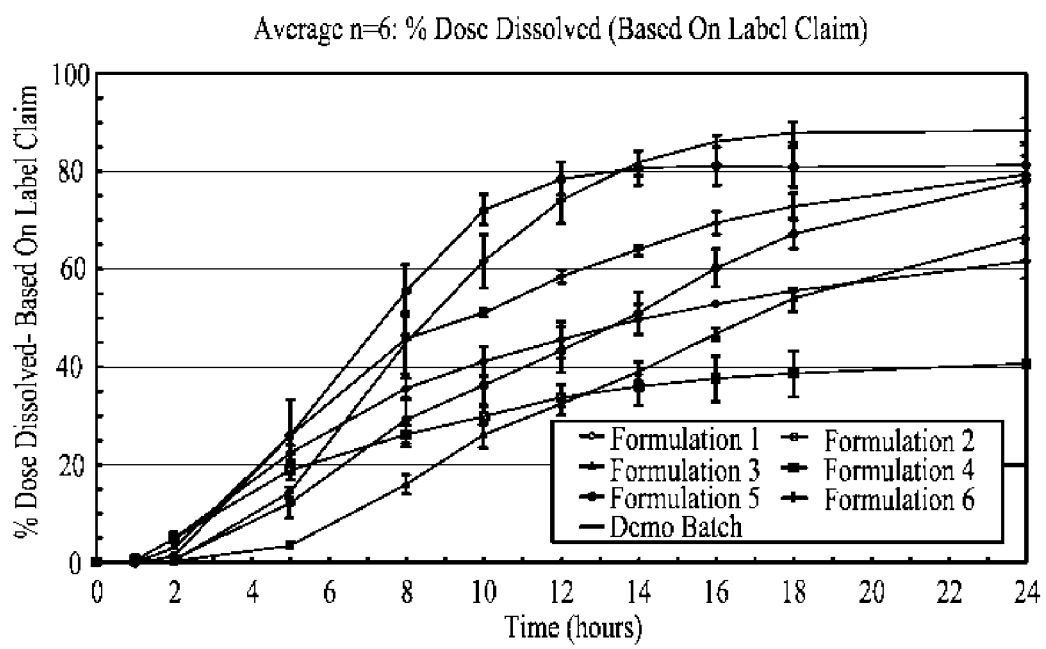
FIG. 8 shows the dissolution of Core Tablet Compositions 7-1 through 7-6.

The results are shown in Table 27 and FIG. 8.

TABLE 27

Dissolution of Core Tablet Compositions Described in Table 26

| Core Tablet Composition | Lag Time (h) | Residual (%) | $t_{70}$ (h) | Zero-order RR (%/h)[1] |
|---|---|---|---|---|
| 7-1 | 1.0 | 38 | NA | 3.8 |
| 7-2 | 2.4 | 22 | 19.5 | 4.9 |
| 7-3 | 4.3 | 33 | NA | 4.5 |
| 7-4 | 0.4 | 59 | NA | 2.2 |
| 7-5 | 2.2 | 19 | 9.8 | 9.3 |
| 7-6 | 3.4 | 12 | 11.3 | 9.5 |

[1]release rate calculated between 5-10 h

As shown in Table 27 and FIG. 8, dissolution at 24 h increases with increasing fraction of high molecular weight PEO in the presence of the osmotic agent in the drug layer. Further, lag time increases with MW of PEO and is shorter in the presence of the osmotic agent in the drug layer. The residual apremilast remaining is highest for Tablet Core Composition 7-4 and decreases for Tablet Core Compositions 7-5 and 7-6 with increasing high molecular weight PEO (600 kDa) fraction and osmotic agent (e.g., NaCl). An overall improvement in dissolution performance for formulations with high MW PWO in the presence of an osmotic agent is observed (7-2 vs. 7-5 and 7-3 vs. 7-6).

Next, core tablet compositions 7-7 through 7-12 were prepared comprising the drug layers shown in Table 28 and same swellable layer as above.

TABLE 28

Core Tablet Compositions 7-7 through 7-12 (100 mg)

| | Core Tablet Comp. | | | | | |
|---|---|---|---|---|---|---|
| | 7-7 | 7-8 | 7-9 | 7-10 | 7-11 | 7-12 |
| Component | Drug Layer Intragranular (% blend) | | | | | |
| 50% APM: HPMCAS-L SDD | 37.5 | 37.5 | 37.5 | 37.5 | 37.5 | 37.5 |
| PEO (300 kDa) | 30.75 | 28.25 | 25.75 | 61.50 | 56.50 | 51.50 |
| PEO (200 kDa) | 30.75 | 28.25 | 25.75 | — | — | — |
| NaCl | — | 5.0 | 10.0 | — | 5.0 | 10.0 |
| Mg stearate | 0.25 | 0.25 | 0.25 | 0.25 | 0.25 | 0.25 |
| Component | Extragranular (% blend) | | | | | |
| cSiO$_2$ | 0.50 | 0.50 | 0.50 | 0.50 | 0.50 | 0.50 |
| Mg stearate | 0.25 | 0.25 | 0.25 | 0.25 | 0.25 | 0.25 |

The dissolution of compositions 7-7 through 7-12 were evaluated using the same conditions as above.

Figure 9:
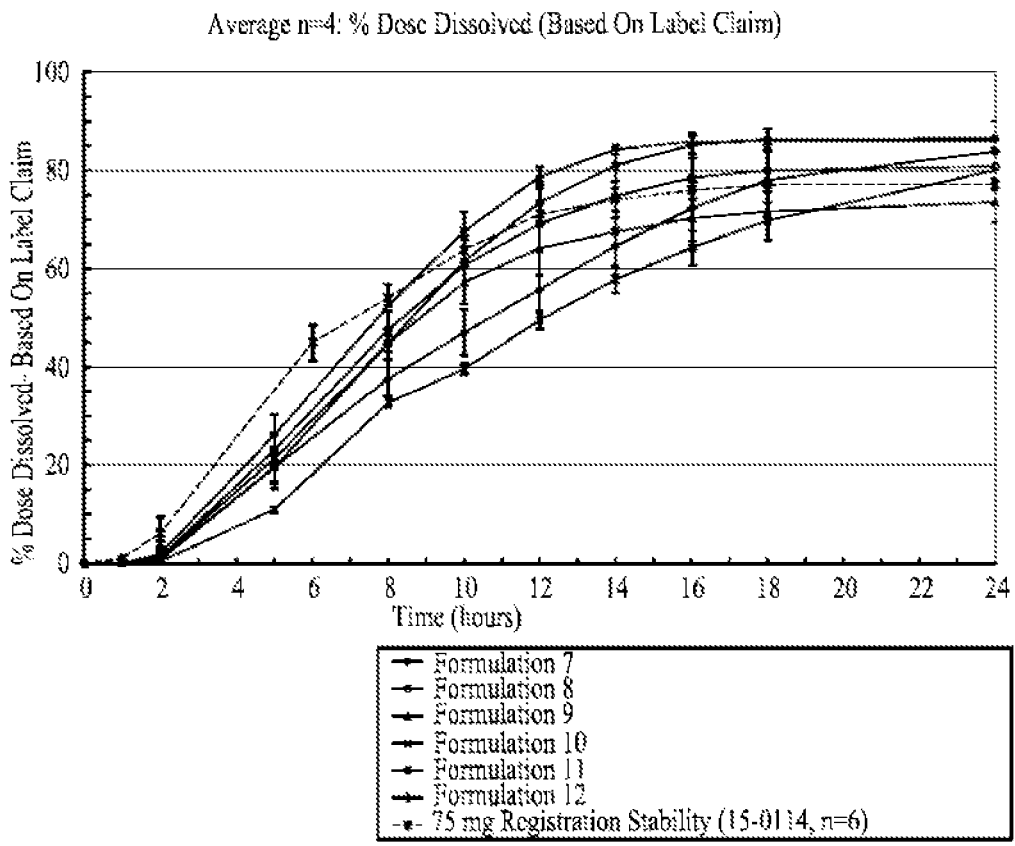
FIG. 9 shows the dissolution of Core Tablet Compositions 7-7 through 7-12.

The results are shown in Table 29 and FIG. 9.

TABLE 29

Dissolution of Core Tablet Compositions Described in Table 28

| Core Tablet Composition | Lag Time (h) | Residual (%) | $t_{70}$ (h) | Zero-order RR (%/h)[1] |
|---|---|---|---|---|
| 7-7 | 1.4 | 16 | 15.2 | 5.8 |
| 7-8 | 1.9 | 19 | 11.5 | 7.5 |
| 7-9 | 2 | 27 | 13.7 | 7.0 |
| 7-10 | 2.9 | 20 | 17.7 | 5.2 |
| 7-11 | 2.7 | 14 | 11.0 | 7.6 |
| 7-12 | 1.9 | 14 | 10.3 | 8.3 |

[1]release rate calculated between 5-10 h

As shown in Table 29 and FIG. 9, both lag time and % residual apremilast remaining increase with increasing osmotic agent in the drug layer for in Compositions 7-7 through 7-9, containing a mixture of the two PEO grades. Lag time and residual apremilast decrease or remain the same with increasing osmotic agent for Compositions with high MW PEO (7-10 through 7-12). Composition 7-12 exhibited desirable performance with the lowest amount of residual apremilast and a short lag time while comprising a single grade of PEO and 10% NaCl.

In general, the minimization of residuals during dissolution was a function of both the concentration of sodium chloride and molecular weight of the PEO in the drug layer, with the lowest residuals found in the formulation with 10% sodium chloride and highest MW PEO (PolyOx WSR 205, MW=600 kDa). Increased amounts of sodium chloride (5% and 10% of drug layer) decrease the lag time and increase release rate for compositions with high MW PEO (7-3 vs 7-6 and 7-10 to 7-12). The shortest lag time was observed in the formulation with 10% NaCl and lowest molecular weight PEO (PolyOx WSR N80, MW=200 kDa). The desirable formulation would reduce residuals and lag time with the simplest formulation; therefore, Formulation 7-12 was the best overall performer from both Round 1 and Round 2 with a lag time of 1.9 h, residuals of 14%, and using only one grade of PEO (PolyOx WSR N750 LEO) with 10% sodium chloride.

Figure 10A:
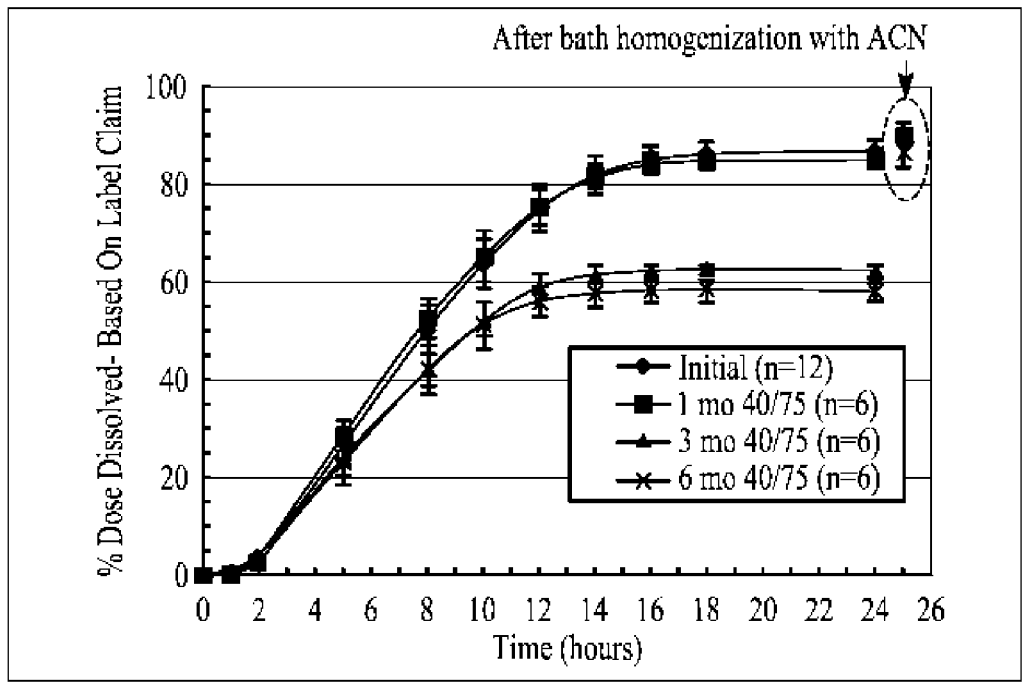
FIG. 10A shows decreased dissolution of Core Tablet Composition 7-8 after various storage conditions.
Figure 10B:
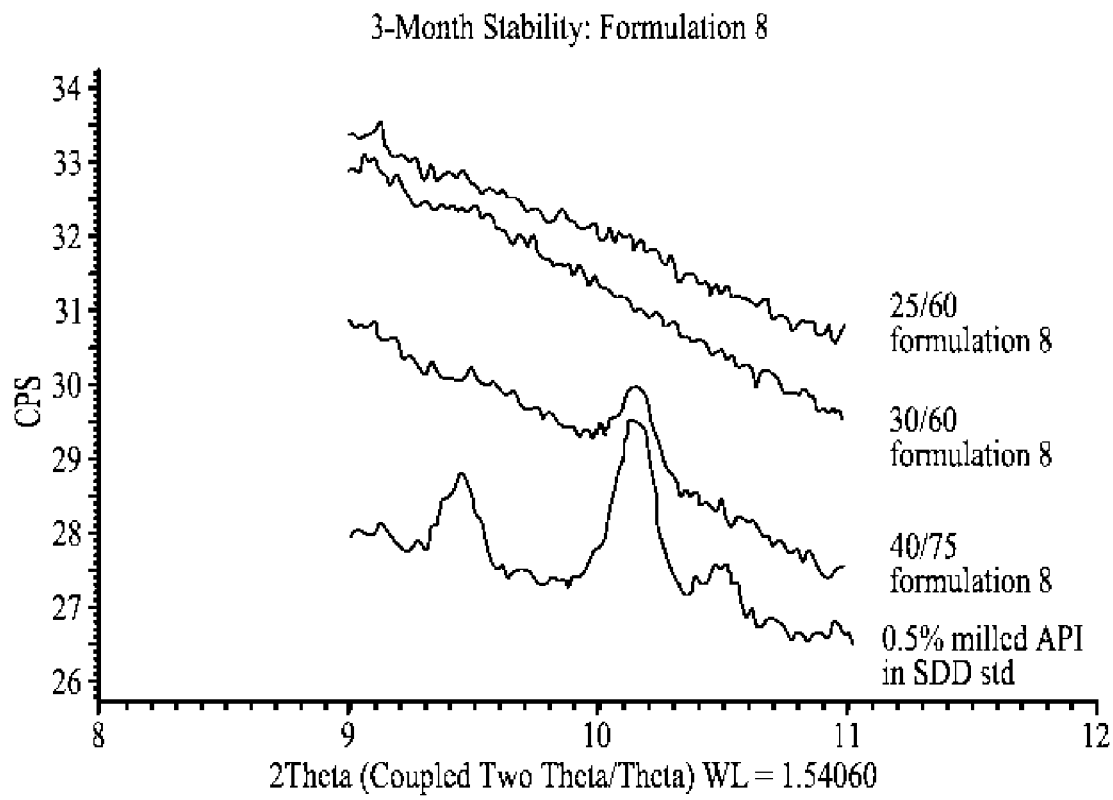
FIG. 10B shows increased crystallinity in Core Tablet Composition 7-8 after various storage conditions.
Figure 11A:
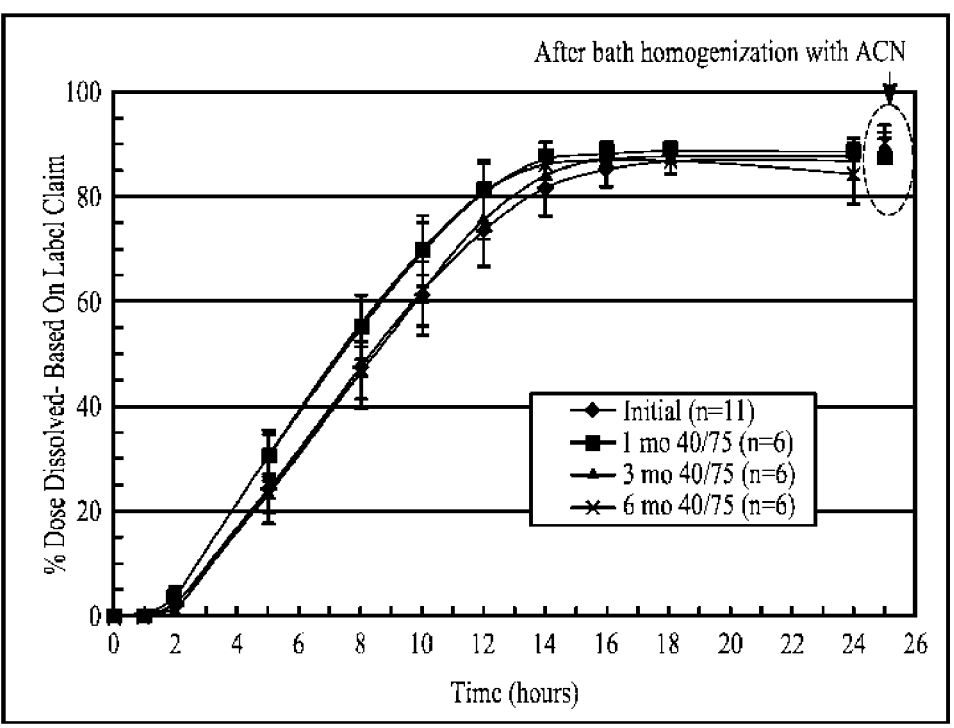
FIG. 11A shows dissolution of Core Tablet Compositions 7-12 after various storage conditions.
Figure 11B:
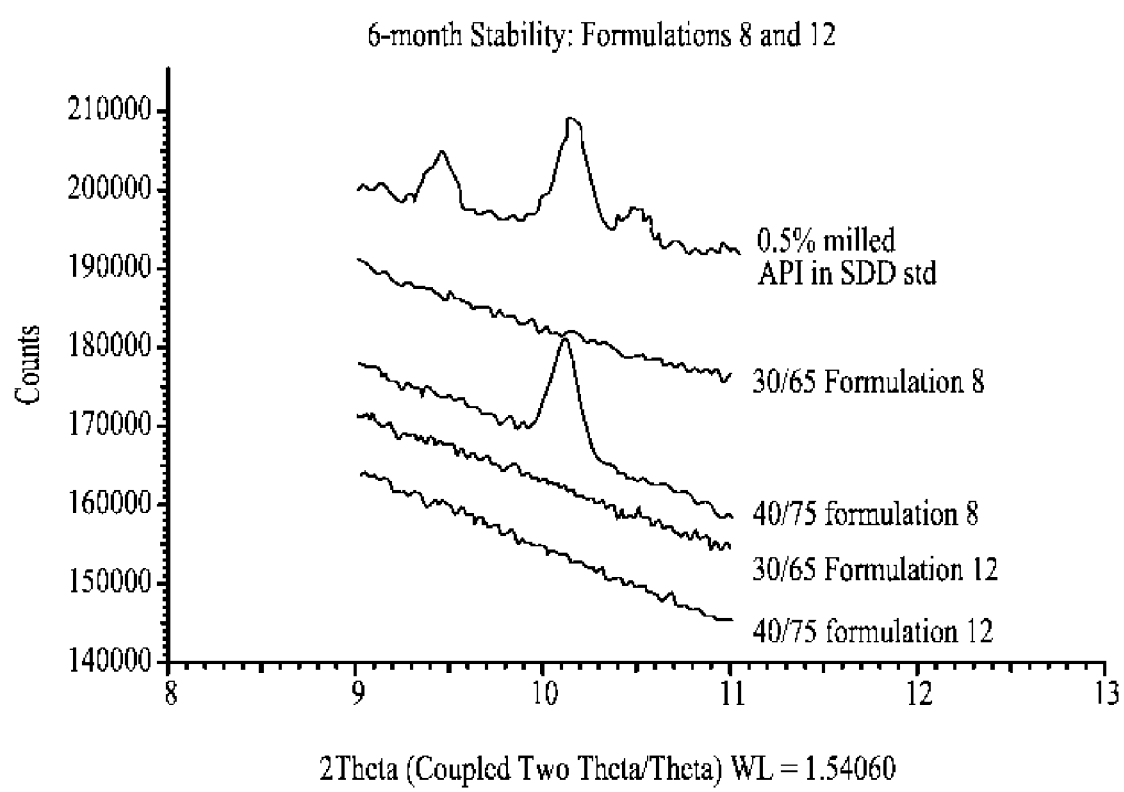
FIG. 11B shows comparison of crystallinity in Core Tablet Composition 7-8 and 7-12 after various storage conditions.

In stability studies, core tablet formulation 7-8 showed some degree of crystallinity by PXRD and decreased dissolution after 3 months and 6 months at 40° C./75% relative humidity (FIGS. 10A and 10B). In contrast, core tablet composition 7-12 showed no crystallinity or changes in dissolution after 6 months at 40° C./75% RH (FIGS. 11A and 11B). Core tablet composition 7-8 showed no changes at 30° C./65% RH at 3-months or 6-months (FIGS. 10B and 11B). In order to ensure the sensitivity of PXRD method to detect crystalline drug in the formulation samples on stability, 0.5% milled API in SDD standard was used as a control in these measurements (FIGS. 10B and 11B).

No changes in dissolution or crystallinity were observed for 7-8 and 7-12 at 25° C./60% RH and 30° C./65% RH while 7-12 remained stable under these conditions. It was determined that undissolved drug in the dissolution medium in combination with residual in the tablet account for the difference in % dose dissolved for samples with decreased performance (approximately 10-15% residual drug in tablet shell is expected for this formulation) (FIG. 10A). Acetonitrile (ACN) was added after the 24 hour timepoint and bath homogenization in order to ensure complete dissolution of the residual drug in the tablet (FIGS. 10A and 11A).

These data demonstrate that high MW PEO in the drug layer is beneficial to ensure adequate dissolution performance at accelerated stability conditions of 30° C./65% RH and 40° C./75% RH. The presence of NaCl in the drug layer in these situations ensures adequate lag time.

The foregoing examples are merely illustrative of embodiments of the disclosed processes described herein and are not intended to limit the disclosed methods. Variations and changes which are obvious to one skilled in the art are intended to be within the scope and nature of the disclosure which is defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing embodiments of the disclosure (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

What is claimed:

1. An oral dosage form comprising:
   a. a core tablet comprising
      (i) a drug layer comprising a) amorphous apremilast and hypromellose acetate succinate (HPMCAS) in a solid dispersion and b) a water soluble polymer; and
      (ii) a swellable layer comprising one or more swellable polymers; and
   b. a coating layer disposed on the core tablet,
   wherein the amorphous apremilast and HPMCAS are present in a weight ratio of 45:55 to 55:45 in the core tablet and the oral dosage form surface comprises at least one drug release orifice.

2. The oral dosage form of claim 1, wherein the apremilast is present in an amount of 6-15 wt % of the core tablet.

3. The oral dosage form of claim 1, wherein the HPMCAS is present in an amount of 6-15 wt % of the core tablet.

4. The oral dosage form of claim 1, wherein apremilast and HPMCAS are present in a weight ratio of 48:52 to 52:48 in the core tablet.

5. The oral dosage form of claim 1, wherein the water soluble polymer comprises polyethylene oxide having an average molecular weight of 200 kDa or higher.

6. The oral dosage form of claim 5, wherein the polyethylene oxide has an average molecular weight of 200-600 kDa.

7. The oral dosage form of claim 1, wherein the water soluble polymer is present in an amount of 30-55 wt % of the core tablet.

8. The oral dosage form of claim 1, wherein the water soluble polymer and apremilast are present in a weight ratio of 2 to 6:1, in the drug layer.

9. The oral dosage form of claim 1, wherein the drug layer further comprises one or more of an osmotic agent, a diluent, and a lubricant.

10. The oral dosage form of claim 9, wherein the drug layer comprises an osmotic agent.

11. The oral dosage form of claim 10, wherein the osmotic agent comprises sodium chloride.

12. The oral dosage form of claim 11, wherein the osmotic agent is present in the drug layer in an amount of 3-8 wt % of the core tablet.

13. The oral dosage form of claim 5, wherein the swellable polymer comprises polyethylene oxide.

14. The oral dosage form of claim 13, wherein the polyethylene oxide of the swellable layer has a higher average molecular weight of the polyethylene oxide in the drug layer.

15. The oral dosage form of claim 13, wherein the polyethylene oxide of the swellable layer has an average molecular weight of 5,000 kDa.

16. The oral dosage form of claim 1, wherein the swellable layer further comprises one or more of an osmotic agent, a diluent, and a lubricant.

17. The oral dosage form of claim 16, wherein the swellable layer comprises an osmotic agent.

18. The oral dosage form of claim 17, wherein the osmotic agent comprises sodium chloride.

19. The oral dosage form of claim 1, wherein the drug layer and swellable layer are present in a weight ratio of 2:1 in the core tablet.

\* \* \* \* \*